(12) United States Patent
Meerovich et al.

(10) Patent No.: US 11,154,619 B2
(45) Date of Patent: Oct. 26, 2021

(54) LIPOSOMAL COMPOSITIONS WITH LIGHT ILLUMINATION-INDUCED DRUG RELEASE

(71) Applicant: Creighton University, Omaha, NE (US)

(72) Inventors: Igor Meerovich, Omaha, NE (US); Alekha Dash, Omaha, NE (US); Michael Nichols, Omaha, NE (US); David Smith, Omaha, NE (US)

(73) Assignee: Creighton University, Omaha, NE (US)

( * ) Notice: Subject to any disclaimer, the term of this patent is extended or adjusted under 35 U.S.C. 154(b) by 150 days.

(21) Appl. No.: 15/900,526

(22) Filed: Feb. 20, 2018

(65) Prior Publication Data

US 2018/0243419 A1  Aug. 30, 2018

Related U.S. Application Data

(60) Provisional application No. 62/460,339, filed on Feb. 17, 2017.

(51) Int. Cl.

| | |
|---|---|
| *A61K 41/00* | (2020.01) |
| *A61K 47/69* | (2017.01) |
| *A61K 47/64* | (2017.01) |
| *A61K 47/54* | (2017.01) |
| *A61K 49/00* | (2006.01) |
| *A61K 33/243* | (2019.01) |
| *A61K 31/35* | (2006.01) |
| *A61K 31/40* | (2006.01) |

(52) U.S. Cl.
CPC ........ *A61K 41/0057* (2013.01); *A61K 33/243* (2019.01); *A61K 41/0042* (2013.01); *A61K 47/546* (2017.08); *A61K 47/6455* (2017.08); *A61K 47/6911* (2017.08); *A61K 49/005* (2013.01); *A61K 31/35* (2013.01); *A61K 31/40* (2013.01); *A61K 2300/00* (2013.01)

(58) Field of Classification Search
None
See application file for complete search history.

(56) References Cited

U.S. PATENT DOCUMENTS

| | | | |
|---|---|---|---|
| 6,900,198 B2 | 5/2005 | Malfroy-Camine et al. | |
| 7,005,255 B2 | 2/2006 | Kaddurah-Daouk et al. | |
| 7,033,775 B2 | 4/2006 | Ullman et al. | |
| 7,041,651 B2 | 5/2006 | Petit, II et al. | |
| 2013/0029429 A1* | 1/2013 | Abe | G01N 1/34 436/501 |

FOREIGN PATENT DOCUMENTS

| | | | |
|---|---|---|---|
| WO | WO-2009026112 A2 * | 2/2009 | ............ A61K 38/10 |
| WO | WO 2014/100379 | 6/2014 | |

OTHER PUBLICATIONS

Zeng et al. Doxorubicin-loaded NaYF4:Yb/Tm—TiO2 inorganic photosensitizers for NIR-triggered photodynamic therapy and enhanced chemotherapy in drug-resistant breast cancers. 2015 Biomaterials 57: 93-106. (Year: 2015).*
Bisby et al., "Active uptake of drugs into photosensitive liposomes and rapid release on UV photolysis," Photochem. Photobiol. 72(1): 57-61, 2000.
Carter et al., "Porphyrin-phospholipid liposomes permeabilized by near-infrared light," Nature Comm. 5:3546, 2014.
Snyder et al., "Photodynamic therapy: a means to enhanced drug delivery to tumors," Cancer Res. 63:8126-8131,2003.
Van Bambeke et al., "Biophysical studies and intracellular destabilization of pH-sensitive liposomes," Lipids 3 5(2): 213-223, 2000.
Wymer et al., "Cascade liposomal triggering: light-induced Ca2+ release from diplasmenylcholine liposomes triggers 5 PLA2-catalyzed hydrolysis and contents leakage from DPPC liposomes," Bioconj, Chem. 9(3): 305-308, 1998.

* cited by examiner

*Primary Examiner* — Jennifer Lamberski
(74) *Attorney, Agent, or Firm* — Fish & Richardson P.C.

(57) ABSTRACT

Provided herein is a small molecule delivery system with illumination-induced small molecule release based on the binary combination of charged liposomes containing small molecules and oppositely charged conjugates of a peptide with a photosensitizer attached to one end of peptide chain, providing binding to liposomes and their permeabilization upon light illumination.

31 Claims, 12 Drawing Sheets

Specification includes a Sequence Listing.

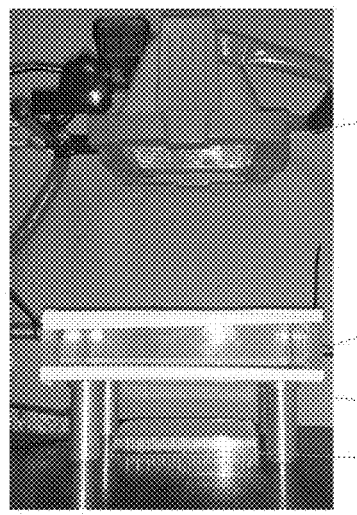 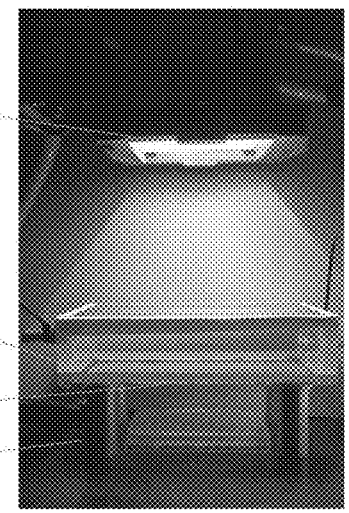
FIG. 1A                                             FIG. 1B

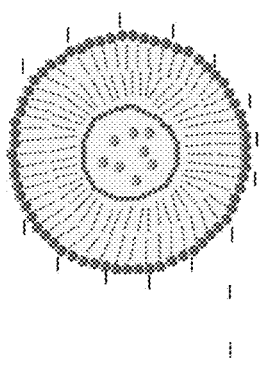

Fig. 9A

Liposomes comprising about 5 to 30% of negatively charged lipid, loaded with drug

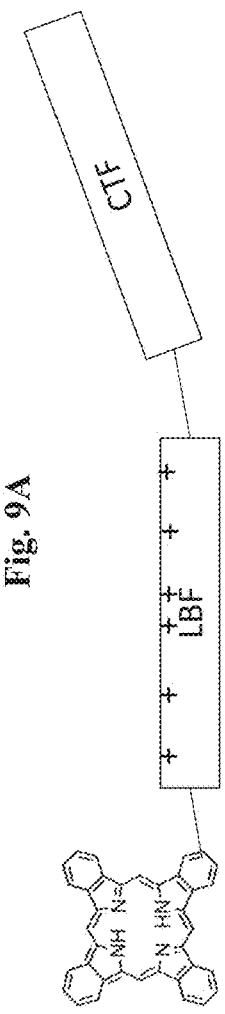

Fig. 9B

Conjugate of a photosensitizer of near-infrared spectral range with a peptide, comprising a positively charged peptide fragment 7-20 amino acid residues long with 30-50% of them arginine ("liposome-binding fragment", LBF) and, optionally, second fragment 4-20 aa long to target cancer cells by specifically binding overexpressed receptors or other molecular groups on their surface ("cancer-targeting fragment", CTF)

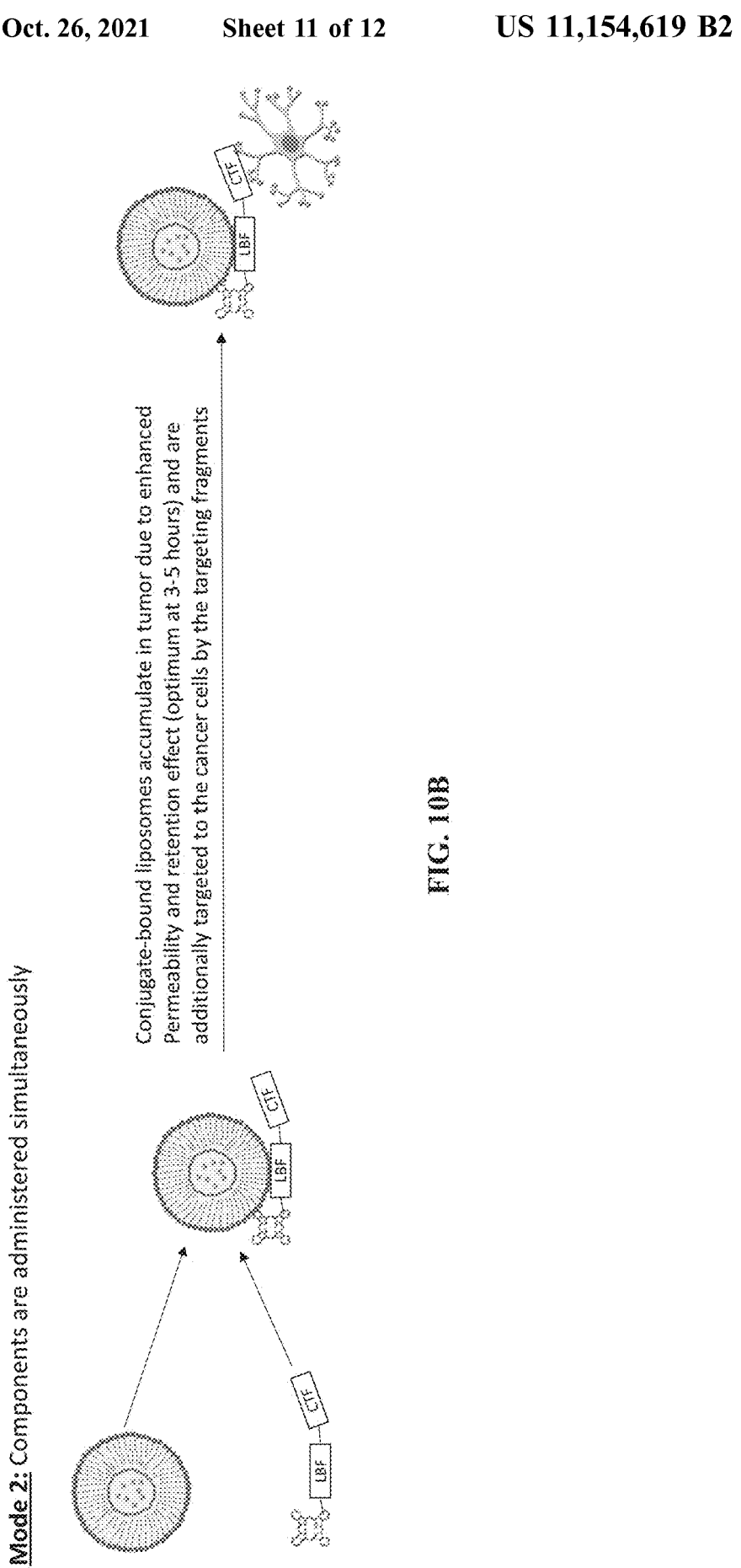

LIPOSOMAL COMPOSITIONS WITH LIGHT ILLUMINATION-INDUCED DRUG RELEASE

RELATED APPLICATIONS

This application claims the benefit of U.S. Provisional Application No. 62/460,339, filed Feb. 17, 2017, which is incorporated herein by reference in its entirety.

TECHNICAL FIELD

The present disclosure relates to a small molecule delivery system with illumination-induced small molecule release based on the binary combination of charged liposomes containing small molecules and oppositely charged conjugates of a peptide with a photosensitizer attached to one end of peptide chain, providing binding to liposomes and release of the small molecules upon light illumination.

BACKGROUND

The delivery of cargo, such as small molecule therapeutic or diagnostic compounds, to target tissues and organs is a central challenge in treating disease. Externally controlled drug release systems hold the potential to selectively enhance localized delivery. Carriers such as liposomes have been developed to improve the biodistribution and efficacy of cargo. However, delivery is often hindered by physiological barriers and release kinetics so that biodistribution and bioavailability are not optimal. To address this problem, strategies have been pursued that make use of external stimuli to trigger local release of the cargo, but it has been challenging to develop a carrier that in physiological conditions can stably retain cargo in the absence of an external stimulus but release it in its presence.

One approach combines the use of a photosensitizer and drug-loaded liposomes for preliminary photodynamic treatment of a pathological area of interest to enhance penetration of the drug (Doxil liposomes) into pathological tissue by an enhanced permeability and retention (EPR) effect (Snyder et al., "Photodynamic therapy: a means to enhanced drug delivery to tumors," (2003) Cancer Res. 63:8126-8131).

Techniques to trigger the release of cargo from liposomes include the photo-triggered cascade-type release of $Ca^{2+}$ ion from liposomes made of synthetic diplasmenylcholine (1,2-dihexadec-1'-enyl-sn-glycero-3-phosphocholine, DPP1sCho) containing $Ca^{2+}$ as a signaling agent for phospholipase $A_2$ (PLA2). A bacteriochlorophyll photosensitizer activates extra-vesicular $PLA_2$ for enzymatic hydrolysis of other marker-loaded liposomes. Wymer et al., "Cascade liposomal triggering: light-induced $Ca^{2+}$ release from diplasmenylcholine liposomes triggers $PLA_2$-catalyzed hydrolysis and contents leakage from DPPC liposomes," (1998) Bioconj. Chem. 9(3):305-308 (Communications). The phototrigger and the drug-loaded liposomes are not separated prior to in vivo administration, leading to the possibility of pre-intended cargo release from the liposome and reduced storage stability of the liposomal component due to potential oxidation.

Use of a photosensitizer-phospholipid conjugate has been proposed as one of the lipid constituents of drug-loaded liposomes intended as a drug delivery vehicle with light-induced drug release based on partial photosensitized oxidation of lipids, which disrupts the stability of the lipid membrane. See WO 2014/100379 and Carter et al., "Porphyrin-phospholipid liposomes permeabilized by near-infrared light," (2014) Nature Comm. 5:3546. The vehicle originally includes both drug load and photosensitizer, thus risking an unintentional release at any time before administration (starting from preparation) unless kept without light. In addition, and similar to many liposomal formulation, the storage stability of these liposomes can be decreased by oxidation of lipids during storage.

Thus, there is a need for a stable liposomal cargo delivery system with controlled cargo release, such as externally controlled cargo release. Additionally, there is a need for methods of targeting tissues and organs for the targeted delivery of cargo using such a system.

SEQUENCE LISTING

The sequence listing associated with this application is provided in text form in lieu of a paper copy and is hereby incorporated by reference into the specification. The name of the text file containing the sequence listing is CORRECTED SEQUENCE LISTING.txt; the text file is 2 KB; was created on Jan. 28, 2021; and is being submitted via EFS-Web on Mar. 25, 2021.

SUMMARY

Provided herein is a method of delivering a small molecule to a target tissue or organ of a subject in need thereof, the method comprising:

a) administering a charged liposomal composition comprising a liposome and a small molecule encapsulated by the liposome;

b) administering a charged peptide composition comprising a peptide chain conjugated to a photosensitizer; and c) applying low intensity light to induce release of the small molecule from the liposome;

wherein the liposomal composition and peptide composition are oppositely charged.

In some embodiments of the method provided herein, the small molecule is a fluorescent marker. In some embodiments, the small molecule is a therapeutic agent. In some embodiments, the therapeutic agent is a chemotherapeutic compound selected from the group consisting of bortezomib, cabozantinib-s-malate, camptothecin, capecitabine, ceritinib, daunorubicin, crizotinib, dabrafenib, dasatinib, degarelix, docetaxel, doxorubicin, doxorubicin hydrochloride, epirubicin, eribulin, etoposide, raloxifene, fulvestrant, methotrexate, pralatrexate, eribulin mesylate, topotecan, ibritumomab tiuxetan, ibrutinib, irinotecan, ixabepilone, cabazitaxel, ado-trastuzumab emtansine, leuprolide acetate, vincristine, mitomycin C, mitoxantrone, nelarabine, paclitaxel, prednisone, eltrombopag olamine, raloxifene hydrochloride, lenalidomide, omacetaxine mepesuccinate, bexarotene, temsirolimus, bendamustine hydrochloride, vinblastine sulfate, vincristine sulfate, vinorelbine tartrate, vorinostat, capecitabine, ipilimumab, goserelin acetate, carboplatin, cisplatin, gemcitabine, calicheamicin, 5-fluorouracil, actinomycin D, cyclophosphamide, vincristine, melphalan, and bleomycin. In some embodiment, the chemotherapeutic compound is about 0.5% to about 10% by weight of the liposomal composition.

In some embodiments of the method provided herein, the peptide chain of the charged peptide composition is from about 7 to about 40 amino acid residues total in length. In some embodiments, the peptide chain is from about 7 to about 20 amino acid residues total in length.

In some embodiments of the method provided herein, the intensity of the low intensity light is from about 10 mW/cm² to about 200 mW/cm².

In some embodiments of the method provided herein, the liposomal composition is negatively charged and the peptide composition is positively charged. In some embodiments, the liposome of the liposomal composition comprises about 5 to about 30 mol % of an anionic phospholipid. In some embodiments, the anionic phospholipid comprises two fatty acid chains that are each independently about 16 to about 20 carbons in length and have about 1 to about 4 double bonds per phospholipid molecule. In some embodiments, the two fatty acid chains are the same. In some embodiments, the two fatty acid chains are different. In some embodiments, the anionic phospholipid is selected from a phosphatidylserine (PS), a phosphatidic acid, a phosphatidylglycerol, a phosphatidylethanolamine, bis(monoacylglycero)phosphate (BMP), and combinations thereof. In some embodiments, the anionic phospholipid is selected from among phosphatidylserine, bis(monoacylglycero)phosphate, 1-stearoyl-2-oleoyl-sn-glycero-3-phosphocholine, 1-stearoyl-2-oleoyl-sn-glycero-3-phosphoserine, and combinations thereof.

In some embodiments of the method provided herein, the small molecule is hydrophilic. In some embodiments, the small molecule is a hydrophilic chemotherapeutic agent. In some embodiments, the chemotherapeutic agent is doxorubicin or doxorubicin hydrochloride. In some embodiments, the small molecule is a hydrophilic fluorescent marker. In some embodiments, the fluorescent marker is calcein.

In some embodiments of the method provided herein, the positively charged peptide comprises amino acids selected from arginine or other guanidinium-containing amino acid residues. In some embodiments, about 30% to about 50% of the amino acid residues of the positively charged peptide are arginine or other guanidinium-containing amino acid residue. In some embodiments, at least 3 of the arginine or other guanidinium-containing amino acid residues are on the same side of the alpha-helix of the positively charged peptide. In some embodiments, the peptide comprises an amino acid sequence having at least 90% sequence identity to the sequence RLARLARRLARLAR (SEQ ID NO:1).

In some embodiments of the method provided herein, the photosensitizer is selected from the group consisting of derivatives of a porphyrin, a metalloporphyrin, a phthalocyanine, a metallophthalocyanine, a chalcogen pyrrillium dye, a pheophorbide, a pyropheophorbide, a pheophytin, a chlorin, a bacteriochlorin, a bacteriopheophorbide, a sapphyrin, a texaphyrin, a purpurin, a porphycene, a phenothiazinium, methylene blue, a xanthene dye, and optionally substituted dimeric or oligomeric porphyrin structures. In some embodiments, the photosensitizer has about 1 to about 8 carboxyl groups. In some embodiments, the photosensitizer has a maximum absorption band in the spectral range of about 660 to 860 nanometers. In some embodiments, the photosensitizer has a quantum yield of singlet oxygen generation above about 0.3. In some embodiments, the photosensitizer is zinc tetracarboxy phthalocyanine.

In some embodiments of the method provided herein, each molecule of the peptide composition comprises about one photosensitizer moiety and about 1 to about 8 peptide chains.

In some embodiments of the method provided herein, the liposomal composition is positively charged and the peptide composition is negatively charged. In some embodiments, the liposome of the liposomal composition comprises about 5 to 30 mol % of a cationic phospholipid.

In some embodiments of the method provided herein, the negatively charged peptide comprises amino acid residues comprising dicarboxylic acid or tricarboxylic acid side chains. In some embodiments, the amino acid residues comprising dicarboxylic acid or tricarboxylic acid side chains comprise about 40% to about 100% of the amino acid residues of the negatively charged peptide. In some embodiments, the peptide comprises 2-amino-4-carboxy-pentanedioic acid. In some embodiments, about 40% to about 100% of the amino acid residues of the negatively charged peptide are 2-amino-4-carboxy-pentanedioic acid.

In some embodiments of the method provided herein, the peptide composition comprises a targeting moiety at the end of the peptide chain opposite the photosensitizer. In some embodiments, the targeting moiety is a peptide comprising about 4 to about 20 amino acid residues. In some embodiments, the targeting moiety peptide comprises amino acid sequences selected from the group consisting of Ala-Glu-Tyr-Leu-Arg (SEQ ID NO:2), Tyr-Glu-Val-His-Thr-Tyr-Tyr-Leu-Asp (SEQ ID NO:3), Tyr-Val-Met-Gly-His-Phe-Arg-Trp-Asp-Arg-Phe (SEQ ID NO:4), Arg-Gly-Asp motif sequences, and Cys-Ser-Lys-Cys (SEQ ID NO: 5) motif sequences. In some embodiments, the targeting moiety is able to bind to cell surface receptors on the target tissue or organ. In some embodiments, the cell surface receptors are overexpressed on cancer cells.

In some embodiments of the method provided herein, the charged liposomal composition and the charged peptide composition are stored separately prior to administration. In some embodiments, the liposomal composition and the peptide composition are stored in lyophilized form.

In some embodiments of the method provided herein, the liposomal composition comprises a hydrophilic antioxidant selected from the group consisting of histidine, histidine derivatives, ascorbic acid, sodium ascorbate, the reduced form of glutathione, and sodium thiosulfate.

In some embodiments of the method provided herein, the liposomal composition and the peptide composition are administered at a ratio of about 40:1 to about 1:1 by weight of the dry compositions.

In some embodiments of the method provided herein, the liposomal composition is administered before the peptide composition is administered. In some embodiments, the liposomal composition is administered about 1 hour to about 6 hours before the peptide composition is administered.

In some embodiments of the method provided herein, the liposomal composition and the peptide composition are administered at the same time.

Also provided herein is a drug delivery kit comprising:
 a charged liposomal composition comprising a liposome and a drug encapsulated by the liposome; and
 a charged peptide composition comprising a peptide chain conjugated to a photosensitizer;
 wherein the liposomal composition and peptide composition are oppositely charged.

In some embodiments of the drug delivery kit provided herein, the small molecule is a fluorescent marker. In some embodiments, the small molecule is a therapeutic agent. In some embodiments, the therapeutic agent is a chemotherapeutic compound selected from the group consisting of bortezomib, cabozantinib-s-malate, camptothecin, capecitabine, ceritinib, daunorubicin, crizotinib, dabrafenib, dasatinib, degarelix, docetaxel, doxorubicin, doxorubicin hydrochloride, epirubicin, eribulin, etoposide, raloxifene, fulvestrant, methotrexate, pralatrexate, eribulin mesylate, topotecan, ibritumomab tiuxetan, ibrutinib, irinotecan, ixabepilone, cabazitaxel, ado-trastuzumab emtansine, leuprolide acetate, vincristine, mitomycin C, mitoxantrone, nelarabine, paclitaxel, prednisone, eltrombopag olamine, raloxifene hydrochloride, lenalidomide, omacetaxine mepesuccinate, bexarotene, temsirolimus, bendamustine hydrochloride, vinblastine sulfate, vincristine sulfate, vinorelbine tartrate, vorinostat, capecitabine, ipilimumab, goserelin acetate, carboplatin, cisplatin, gemcitabine, calicheamicin, 5-fluorouracil, actinomycin D, cyclophosphamide, vincristine, melphalan, and bleomycin. In some embodiments, the chemotherapeutic compound is about 0.5% to about 10% by weight of the liposomal composition.

In some embodiments of the drug delivery kit provided herein, the peptide chain of the charged peptide composition is from about 7 to about 40 amino acid residues total in length. In some embodiments, the peptide chain is from about 7 to about 20 amino acid residues total in length.

In some embodiments of the drug delivery kit provided herein, the liposomal composition is negatively charged and the peptide composition is positively charged. In some embodiments, the liposome of the liposomal composition comprises about 5 to 30 mol % of an anionic phospholipid. In some embodiments, the anionic phospholipid comprises two fatty acid chains that are each independently about 16 to about 20 carbons in length and have about 1 to about 4 double bonds per phospholipid molecule. In some embodiments, the two fatty acid chains are the same. In some embodiments, the two fatty acid chains are different. In some embodiments, the anionic phospholipid is selected from a phosphatidylserine (PS), a phosphatidic acid, a phosphatidylglycerol, a phosphatidylethanolamine, bis(monoacylglycero)phosphate (BMP), and combinations thereof. In some embodiments, the anionic phospholipid is selected from among phosphatidylserine, bis(monoacylglycero)phosphate, 1-stearoyl-2-oleoyl-sn-glycero-3-phosphocholine, 1-stearoyl-2-oleoyl-sn-glycero-3-phosphoserine, and combinations thereof.

In some embodiments of the drug delivery kit provided herein, the small molecule is hydrophilic. In some embodiments, the small molecule is a hydrophilic chemotherapeutic agent. In some embodiments, the chemotherapeutic agent is doxorubicin or doxorubicin hydrochloride. In some embodiments, the small molecule is a hydrophilic fluorescent marker. In some embodiments, the fluorescent marker is calcein.

In some embodiments of the drug delivery kit provided herein, the peptide chain of the positively charged peptide composition comprises amino acids selected from arginine or other guanidinium-containing amino acid residues. In some embodiments, about 30% to about 50% of the amino acid residues of the positively charged peptide are arginine or other guanidinium-containing amino acid residue. In some embodiments, at least 3 of the arginine or other guanidinium-containing amino acid residues are on the same side of the alpha-helix of the positively charged peptide. In some embodiments, the peptide comprises an amino acid sequence having at least 90% sequence identity to the sequence RLARLARRLARLAR (SEQ ID NO:1).

In some embodiments of the method provided herein, the photosensitizer is selected from the group consisting of derivatives of a porphyrin, a metalloporphyrin, a phthalocyanine, a metallophthalocyanine, a chalcogen pyrrilium dye, a pheophorbide, a pyropheophorbide, a pheophytin, a chlorin, a bacteriochlorin, a bacteriopheophorbide, a sapphyrin, a texaphyrin, a purpurin, a porphycene, a phenothiazinium, methylene blue, a xanthene dye, and optionally substituted dimeric or oligomeric porphyrin structures. In some embodiments, the photosensitizer has about 1 to about 8 carboxyl groups. In some embodiments, the photosensitizer has a maximum absorption band in the spectral range of about 660 to 860 nanometers. In some embodiments, the photosensitizer has a quantum yield of singlet oxygen generation above about 0.3. In some embodiments, the photosensitizer is zinc tetracarboxy phthalocyanine.

In some embodiments of the drug delivery kit provided herein, each molecule of the peptide composition comprises about one photosensitizer moiety and about 1 to about 8 peptide chains.

In some embodiments of the drug delivery kit provided herein, the liposomal composition is positively charged and the peptide composition is negatively charged. In some embodiments, the liposome of the liposomal composition comprises about 5 to 30 mol % of a cationic phospholipid.

In some embodiments of the drug delivery kit provided herein, the peptide chain of the negatively charged peptide composition comprises amino acid residues comprising dicarboxylic acid or tricarboxylic acid side chains. In some embodiments, amino acid residues comprising dicarboxylic acid or tricarboxylic acid side chains comprise about 40% to about 100% of the amino acid residues of the negatively charged peptide. In some embodiments, the peptide comprises 2-amino-4-carboxy-pentanedioic acid. In some embodiments, about 40% to about 100% of the amino acid residues of the negatively charged peptide are 2-amino-4-carboxy-pentanedioic acid.

In some embodiments of the drug delivery kit provided herein, the peptide composition comprises a targeting moiety at the end of the peptide chain opposite the photosensitizer. In some embodiments, the targeting moiety is a peptide comprising about 4 to about 20 amino acids. In some embodiments, the targeting moiety peptide comprises amino acid sequences selected from the group consisting of Ala-Glu-Tyr-Leu-Arg (SEQ ID NO:2), Tyr-Glu-Val-His-Thr-Tyr-Tyr-Leu-Asp (SEQ ID NO:3), Tyr-Val-Met-Gly-His-Phe-Arg-Trp-Asp-Arg-Phe (SEQ ID NO:4), Arg-Gly-Asp motif sequences, and Cys-Ser-Lys-Cys (SEQ ID NO: 5) motif sequences. In some embodiments, the targeting moiety is able to bind to cell surface receptors on the target tissue or organ. In some embodiments, the cell surface receptors are overexpressed on cancer cells.

In some embodiments of the drug delivery kit provided herein, the liposomal composition and the peptide composition are stored separately prior to administration to a subject in need thereof.

Other features and advantages of the methods, compositions, and kits provided herein will be apparent from the following detailed description and figures, and from the claims.

DESCRIPTION OF DRAWINGS

FIGS. 1A-1B shows the setup used for illumination of samples for photo-induced release.

FIGS. 9A-9B illustrate an exemplary embodiment of the compositions described herein. FIG. 9A shows an exemplary negatively charged liposomal composition that contains a negatively charged liposome encapsulating a hydrophilic small molecule. FIG. 9B shows a positively charged peptide composition that contains a positively charged peptide chain conjugated to an exemplary photosensitizer and an optional targeting moiety.

FIGS. 10A-10B illustrate an exemplary method of I.V. administration of exemplary compositions described herein. FIG. 10A shows an exemplary embodiment where the liposomal composition is administered prior to the peptide composition. FIG. 10B shows an exemplary embodiment where the liposomal composition and the peptide composition are administered simultaneously.

DETAILED DESCRIPTION

Figure 2A:
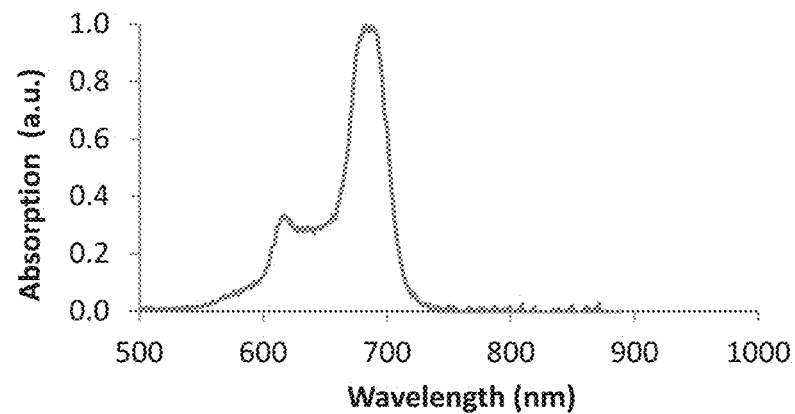
FIGS. 2A-2B show the absorption spectrum of the photosensitizer (FIG. 2A) and the emission spectrum of the illumination setup (FIG. 2B).

Provided herein is a method of delivering a small molecule to a target tissue or organ of a subject in need thereof and compositions useful for the delivery. The methods and compositions allow for controllable, light-induced release of the small molecule from liposomes. The methods and compositions avoid unintended release of the small molecule before reaching the target tissue or organ.

Provided herein is a method of delivering a small molecule to a target tissue or organ of a subject in need thereof and compositions useful for the delivery. The method includes: a) administering a charged liposomal composition that includes a liposome and a small molecule encapsulated by the liposome; b) administering an oppositely charged peptide composition that includes a peptide chain conjugated to a photosensitizer; and c) applying low intensity light to induce release of the small molecule from the liposome. In some embodiments, the method includes forming a noncovalent association between the liposomal composition and the peptide composition. In some embodiments, the liposomal composition and the peptide composition bind each other electrostatically. In some embodiments, the liposomal composition and the peptide composition bind each other electrostatically at the target tissue or organ. In some embodiments, the method includes permeabilization of the drug into a target tissue or organ. The terms "target tissue" and "target organ," as used herein, refer to an intended site for delivery of the small molecule of the compositions provided herein following administration to a subject. For example, the methods disclosed herein can employ a target tissue that is affected with cancer.

Charged Liposomal Composition

In the methods provided herein, the method includes administration of a charged liposomal composition that includes a liposome and a small molecule encapsulated by the liposome. In some embodiments, the small molecule is an imaging agent, a diagnostic agent, a therapeutic agent, or a combination thereof. As used herein, the term "small molecule" refers to a low molecular-weight pharmaceutical, therapeutic, diagnostic, and/or imaging agent (examples of the latter being fluorescent markers, dyes, etc.), that has a molecular weight of less than about 10 kD, such as less than about 5000 Daltons, or less than about 1000 Daltons, for example about 100 to about 900 Daltons, about 200 to about 800 Daltons, about 300 to about 700 Daltons, about 400 to about 600 Daltons, or about 500 Daltons. In some embodiments, the small molecule can be a salt, ester, and/or other pharmaceutically acceptable form of such compounds.

In some embodiments, the liposomal composition contains small molecules, such as diagnostic, imaging, and/or therapeutic agents, encapsulated within the interior of the liposome, contained within the hydrocarbon chain region of the bilayer, complexed/associated with the inner and/or outer monolayer (e.g., via static interaction or chemical/covalent interaction), or a combination thereof. Examples of small molecules include compounds useful for treating patients that are suffering from (e.g., diagnosed with) or pre-disposed to any disease state, including, but not limited to, cancers (e.g., a breast cancer, an uterine cancer, an ovarian cancer, a prostate cancer, a testicular cancer, a lung cancer, an ocular cancer, e.g., retinoblastoma or uveal melanoma, a leukemia, a lymphoma, a colon cancer, a gastrointestinal cancer, a pancreatic cancer, a bladder cancer, a kidney cancer, a bone cancer, a neurological cancer, a head and neck cancer, a skin cancer, a sarcoma, an adenoma, a carcinoma, and a myeloma); and infectious diseases (e.g., bacterial diseases, fungal diseases, parasitic diseases and viral diseases (such as a viral hepatitis, a disease caused by a cardiotropic virus; HIV/AIDS, flu, SARS, and the like)).

In some embodiments, the small molecule is a therapeutic agent useful for the treatment of cancer, for example, a chemotherapeutic compound. Examples of chemotherapeutic compounds include, but are not limited to bortezomib, cabozantinib-s-malate, camptothecin, capecitabine, ceritinib, daunorubicin, crizotinib, dabrafenib, dasatinib, degarelix, docetaxel, doxorubicin, doxorubicin hydrochloride, epirubicin, eribulin, etoposide, raloxifene, fulvestrant, methotrexate, pralatrexate, eribulin mesylate, topotecan, ibritumomab tiuxetan, ibrutinib, irinotecan, ixabepilone, cabazitaxel, ado-trastuzumab emtansine, leuprolide acetate, vincristine, mitomycin C, mitoxantrone, nelarabine, paclitaxel, prednisone, eltrombopag olamine, raloxifene hydrochloride, lenalidomide, omacetaxine mepesuccinate, bexarotene, temsirolimus, bendamustine hydrochloride, vinblastine sulfate, vincristine sulfate, vinorelbine tartrate, vorinostat, capecitabine, ipilimumab, goserelin acetate, carboplatin, cisplatin, gemcitabine, calicheamicin, 5-fluorouracil, actinomycin D, cyclophosphamide, vincristine, melphalan, and bleomycin. In some embodiments, the chemotherapeutic compound is doxorubicin. In some embodiments, the chemotherapeutic compound is doxorubicin hydrochloride.

In some embodiments, the small molecule is a fluorescent marker or other imaging agent. Accordingly, provided herein are compositions and methods wherein release of the small molecule from the liposome is detected by a detectable change. For example, small molecule release can give rise to a color change which is observed with the naked eye or spectroscopically. Methods for visualizing the detectable change resulting from release of the small molecule from the liposome include any fluorescent detection method, including, but not limited to fluorescence microscopy, a microtiter plate reader, or fluorescence-activated cell sorting (FACS).

Examples of fluorescent markers and other imaging agents include any of the fluorophores described herein as well as other detectable labels known in the art, including, but not limited to, redox active probes, chemiluminescent molecules, radioactive labels, dyes, fluorescent molecules, phosphorescent molecules, imaging and/or contrast agents, quantum dots, as well as any marker which can be detected using spectroscopic means, i.e., those markers detectable using microscopy and cytometry. Suitable fluorescent markers include any fluorescent marker with absorption outside the spectral range of the illumination light.

In some embodiments, the fluorescent marker is selected from among fluorescent polypeptides, FITC, R-phycoerythrin (PE), PE-Texas Red Tandem, PE-Cy5 Tandem, EGFP, EYGP, ECF, DsRed, allophycocyanin (APC), PerCp, SYTOX Green, coumarin, Alexa Fluors dyes (e.g., 350, 430, 488, 532, 546, 555, 568, 594, 633, 647, 660, 680, 700, 750), cyanine dyes (e.g., Cy2, Cy3, Cy3.5, Cy5, Cy5.5, Cy7), Hoechst 33342, DAPI, Hoechst 33258, SYTOX Blue, chromomycin A3, mithramycin, YOYO-1, SYTOX Orange, ethidium bromide, 7-AAD, acridine orange, TOTO-1, TO-PRO-1, thiazole orange, TOTO-3, TO-PRO-3, propidium iodide (PI), LDS 751, Indo-1, Fluo-3, DCFH, DHR, SNARF, Y66F, Y66H, EBFP, GFPuv, ECFP, GFP, AmCyan1, Y77W, S65A, S65C, S65L, S65T, ZsGreen1, ZsYellow1, DsRed2, DsRed monomer, AsRed2, mRFP1, HcRed1, monochlorobimane, calcein, the DyLight Fluors, cyanine, hydroxycoumarin, aminocoumarin, methoxycoumarin, Cascade Blue, Lucifer Yellow, NBD, PE-Cy5 conjugates, PE-Cy7 conjugates, APC-Cy7 conjugates, Red 613, fluorescein, Fluor X, BODIDY-FL, TRITC, X-rhodamine, Lissamine Rhodamine B, Texas Red, TruRed, and derivatives thereof. In some embodiments, the fluorescent marker is hydrophilic. In some embodiments, the fluorescent marker is calcein.

Methods of labeling biomolecules with fluorescent molecules and measuring fluorescence are well known in the art.

Examples of other suitable small molecules are well known and easily identified by those skilled in the art, and many can be found on databases such as Pharmabase (National Center for Research Sources, National Institutes of Health). General classes of pharmaceutical small molecules include, but are not limited to, compounds involved in regulating membrane transport (e.g., channels, pumps, receptors, transporters); compounds involved in metabolism (such as ATP inhibitors, electron transport controllers, inhibitors of amino acid or fatty acid synthesis, ceramide analogs, etc.); intracellular messengers (e.g., kinase inhibitors, etc.); compounds involved in regulating cell signaling; compounds involved in regulating cellular area; as well as other well-known classes of small molecules. Additional examples of small molecule classes and compounds can be found throughout U.S. Pat. Nos. 7,041,651; 7,033,775; 7,005,255; and 6,900,198; the disclosures of each of which are incorporated by reference herein in their entireties.

In some embodiments, the small molecule has a pKa of about 2 to about 9. In some embodiments, the small molecule has several pKas (e.g., 2, 3, and 4) within this range. In some embodiments, the small molecule can be water-soluble, slightly water-soluble, or poorly water soluble (including compounds that are not soluble in water). In some embodiments, the small molecule is hydrophobic. In some embodiments, the small molecule is hydrophilic.

In some embodiments of the methods and provided herein, the liposomal composition is negatively charged. In some embodiments, the liposomal composition is negatively charged and the peptide composition is positively charged. In some embodiments, the negatively charged liposomal composition includes liposomes comprising anionic phospholipids. In some embodiments, the anionic phospholipid contains two fatty acid chains. In some embodiments, the fatty acid chains are the same. In some embodiments, the fatty acid chains are different. In some embodiments, the anionic phospholipid contains two fatty acid chains that are each independently about 10 to about 25 carbons in length, for example, about 10 to about 20, about 10 to about 16, about 16 to about 20 carbons in length, or about 10, 11, 12, 13, 14, 15, 16, 17, 18, 19, 20, 21, 22, 23, 24, or about 25 carbons in length. In some embodiments, the fatty acid chains each independently have about 1 to about 6 double bonds per phospholipid molecule, such as about 1 to about 5, about 1 to about 4, about 1 to about 3, about 1 to about 2, about 2 to about 6, about 2 to about 5, about 2 to about 4, about 2 to about 3, about 3 to about 6, about 3 to about 5, about 3 to about 4, about 4 to about 6, about 4 to about 5, or about 5 to about 6 double bonds per phospholipid molecule. In some embodiments, the anionic phospholipid contains two fatty acid chains that are each independently about 16 to about 20 carbons in length and have about 1 to about 4 double bonds per phospholipid molecule.

In some embodiments, the anionic phospholipid is selected from among a a phosphatidylserine (PS), a phosphatidic acid, a phosphatidylglycerol, a phosphatidylethanolamine, bis(monoacylglycero)phosphate (BMP), and combinations thereof. In some embodiments, the anionic phospholipid is selected from among phosphatidylserine, bis(monoacylglycero)phosphate, 1-stearoyl-2-oleoyl-sn-glycero-3-phosphocholine, 1-stearoyl-2-oleoyl-sn-glycero-3-phsphoserine, and combinations thereof. In some embodiments, the liposome includes 1-stearoyl-2-oleoyl-sn-glycero-3-phosphocholine and 1-stearoyl-2-oleoyl-sn-glycero-3-phsphoserine. In some embodiments, the liposome further includes cholesterol. In some embodiments, the liposome comprises phosphatidylserine. In some embodiments, the liposome comprises bis(monoacylglycero)phosphate.

In some embodiments, the liposome of the negatively charged liposomal composition includes liposomes comprising anionic phospholipids in an amount of about 5 mol % to about 30 mol % of the liposome. For example, the liposome contains about 5 mol % to about 25 mol %, about 5 mol % to about 20 mol %, about 5 mol % to about 15 mol %, about 5 mol % to about 10 mol %, about 10 mol % to about 30 mol %, about 10 mol % to about 25 mol %, about 10 mol % to about 20 mol %, about 10 mol % to about 15 mol %, about 15 mol % to about 30 mol %, about 15 mol % to about 25 mol %, about 15 mol % to about 20 mol %, about 20 mol % to about 30 mol %, about 20 mol % to about 25 mol %, or about 25 mol % to about 30 mol % anionic phospholipid.

In some embodiments, the liposomal composition is negatively charged and comprises a liposome that includes anionic phospholipids and encapsulates a hydrophilic small molecule. In some embodiments, the hydrophilic small molecule is a hydrophilic chemotherapeutic agent. In some embodiments, the hydrophilic chemotherapeutic agent is doxorubicin or doxorubicin hydrochloride. In some embodiments, the hydrophilic small molecule is a hydrophilic fluorescent marker. In some embodiments, the hydrophilic fluorescent marker is calcein.

In some embodiments of the methods and compositions provided herein, the liposomal composition is positively charged. In some embodiments, the liposomal composition is positively charged and the peptide composition is negatively charged. In some embodiments, the positively charged liposomal composition includes liposomes comprising cationic lipids, such as cationic phospholipids. Examples of suitable cationic lipids and phospholipids include, but are not limited to phosphatidylethanolamine, dioleoylphosphatidylethanolamine (DOPE), an amine derivative of phosphatidylcholine, stearylamine, 1,2-diacyl-3-trimethylammonium-propane (TAP), 1,2-triacyl-3-dimethylammonium-propane (DAP), 1,2-dimyri stoyl-3-trimethylammonium-propane (DMTAP), esters of phosphatidic acid and amino alcohol, such as an ester of dipalmitoyl phosphatidic acid (DPPA), distearoyl phosphatidic acid, hydroxyethylenediamine, 1,2-dioleoyloxy-3-(trimethylammonium)propane (DOTAP), N,N-dioctadecylamidoglycylspermine (DOGS), dimethyloctadecylammonium bromide (DDAB), N-[1-(2,3-dioleyloxy)propyl]-N,N,N-trimethylammonium chloride (DOTMA), 2,3-dioleyloxy-N-[2(spermine-carboxamido)ethyl]-N,N-dimethyl-1-propaneami-niumtrifluoroacetate (DOSPA), and N-[1-(2,3-dimyristyloxy)propyl]-N,N-dimethyl-N-(2-hydroxyethyl)ammonium bromide (DMRIE). In some embodiments, the cationic liposomes include cholesterol.

In some embodiments, the liposome of the positively charged liposomal composition includes liposomes comprising cationic lipids or phospholipids in an amount of about 5 mol % to about 30 mol % of the liposome. For example, the liposome contains about 5 mol % to about 25 mol %, about 5 mol % to about 20 mol %, about 5 mol % to about 15 mol %, about 5 mol % to about 10 mol %, about 10 mol % to about 30 mol %, about 10 mol % to about 25 mol %, about 10 mol % to about 20 mol %, about 10 mol % to about 15 mol %, about 15 mol % to about 30 mol %, about 15 mol % to about 25 mol %, about 15 mol % to about 20 mol %, about 20 mol % to about 30 mol %, about 20 mol % to about 25 mol %, or about 25 mol % to about 30 mol % cationic phospholipid.

In some embodiments, the liposomal composition is positively charged and comprises a liposome that includes cationic phospholipids and encapsulates a hydrophobic small molecule.

In some embodiments of the methods provided herein, the small molecules are suitably encapsulated, contained, or complexed/associated with the liposomes described herein by mixing the one or more small molecules with the liposomes during processing. Suitable ratios of small molecule:liposome are readily determined by the ordinarily skilled artisan. The ratio of the lipids can be varied to optimize the efficiency of uptake of the small molecule for the specific target cell type.

In some embodiments, the small molecule is about 0.5% to about 10% by weight of the liposomal composition, for example, about 0.5% to about 9%, about 0.5% to about 8%, about 0.5% to about 7%, about 0.5% to about 6%, about 0.5% to about 5%, about 0.5% to about 4%, about 0.5% to about 3%, about 0.5% to about 2%, about 0.5% to about 1%, about 1% to about 10%, about 1% to about 9%, about 1% to about 8%, about 1% to about 7%, about 1% to about 6%, about 1% to about 5%, about 1% to about 4%, about 1% to about 3%, about 1% to about 2%, about 2% to about 10%, about 2% to about 9%, about 2% to about 8%, about 2% to about 7%, about 2% to about 6%, about 2% to about 5%, about 2% to about 4%, about 2% to about 3%, about 3% to about 10%, about 3% to about 9%, about 3% to about 8%, about 3% to about 7%, about 3% to about 6%, about 3% to about 5%, about 3% to about 4%, about 4% to about 10%, about 4% to about 9%, about 4% to about 8%, about 4% to about 7%, about 4% to about 6%, about 4% to about 5%, about 5% to about 10%, about 5% to about 9%, about 5% to about 8%, about 5% to about 7%, about 5% to about 6%, about 6% to about 10%, about 6% to about 9%, about 6% to about 8%, about 6% to about 7%, about 7% to about 10%, about 7% to about 9%, about 7% to about 8%, about 8% to about 10%, about 8% to about 9%, or about 9% to about 10% by weight of the liposomal composition. In some embodiments, the small molecule is a chemotherapeutic compound. In some embodiments, the small molecule is a chemotherapeutic compound and is about 0.5% to about 10% by weight of the liposomal composition.

Charged Peptide Composition

In the methods provided herein, the method includes administration of a charged peptide composition that includes a peptide chain conjugated to a photosensitizer. As used herein, the term "photosensitizer" refers to an activatable compound that produces a signal when activated by light. The photosensitizers provided herein can produce a photochemical or phototoxic effect on a cell when light activated, for example, produce a reactive species when light activated. In some embodiments, the photosensitizer is hydrophobic. In some embodiments, the photosensitizer is hydrophilic. Examples of suitable photosensitizers include, but are not limited to, derivatives of a porphyrin, a metalloporphyrin, a phthalocyanine, a metallophthalocyanine, a chalcogen pyrrillium dye, a pheophorbide, a pyropheophorbide, a pheophytin, a chlorin, a bacteriochlorin, a bacteriopheophorbide, a sapphyrin, a texaphyrin, a purpurin, a porphycene, a phenothiazinium, methylene blue, a xanthene dye, and dimeric or oligomeric porphyrin structures optionally substituted with an organic group. In some embodiments, the photosensitizer is a phthalocyanine. In some embodiments, the photosensitizer is zinc tetracarboxy phthalocyanine. In some embodiments, the photosensitizer is stable to trifluoroacetic acid.

In some embodiments, the photosensitizer is conjugated to the peptide using similar chemical techniques as those used for solid-phase peptide synthesis. In some embodiments, the photosensitizer is conjugated to the peptide through an amide bond. In some embodiments, the photosensitizer has about 1 to about 10 carboxyl groups, such as about 1 to about 8, 1 to about 5, 1 to about 3, 3 to about 10, 3 to about 8, 3 to about 5, 5 to about 10, 5 to about 8, 8 to about 10, or about 1, 2, 3, 4, 5, 6, 7, 8, 9, or 10 carboxyl groups. In some embodiments, the photosensitizer has about 1 to about 8 carboxyl groups. In some embodiments, the photosensitizer has about 1 carboxyl group.

In some embodiments, the photosensitizer has a maximum absorption band in the near-infrared spectral range. In some embodiments, the photosensitizer has a maximum absorption band in the spectral range of about 660 to about 860 nanometers (nm), such as about 660 nm to about 800 nm, about 660 nm to about 760 nm, about 660 nm to about 700 nm, about 700 nm to about 860 nm, about 700 nm to about 800 nm, about 700 nm to about 760 nm, about 760 nm to about 860 nm, about 760 nm to about 800 nm, or about 800 nm to about 860 nm.

In some embodiments, the photosensitizer has a moderate or high quantum yield of singlet oxygen generation. For example, the photosensitizer has a quantum yield of singlet oxygen generation of above about 0.3, such as about 0.3, 0.4, 0.5, 0.6, 0.7, 0.8, or about 0.9. In some embodiments, the quantum yield is above about 0.3. In some embodiments, the quantum yield is about 0.3 to about 0.9.

In some embodiments, each molecule of the charged peptide composition comprises about 1 to about 5 photosensitizer moieties, such as about 1 to about 4, about 1 to about 3, about 1 to about 2, about 2 to about 5, about 2 to about 4, about 2 to about 3, about 3 to about 5, about 3 to about 4, about 4 to about 5, or about 1, 2, 3, 4, or 5 photosensitizer moieties. In some embodiments, each molecule of the charged peptide composition comprises about 1 photosensitizer moiety. In some embodiments, each molecule of the charged peptide composition comprises about 1 to about 10 peptide chains, such as about 1 to about 9, about 1 to about 8, about 1 to about 7, about 1 to about 6, about 1 to about 5, about 1 to about 4, about 1 to about 3, about 1 to about 2, about 2 to about 10, about 2 to about 9, about 2 to about 8, about 2 to about 7, about 2 to about 6, about 2 to about 5, about 2 to about 4, about 2 to about 3, about 3 to about 10, about 3 to about 9, about 3 to about 8, about 3 to about 7, about 3 to about 6, about 3 to about 5, about 3 to about 4, about 4 to about 10, about 4 to about 9, about 4 to about 8, about 4 to about 7, about 4 to about 6, about 4 to about 5, about 5 to about 10, about 5 to about 9, about 5 to about 8, about 5 to about 7, about 5 to about 6, about 6 to about 10, about 6 to about 9, about 6 to about 8, about 6 to about 7, about 7 to about 10, about 7 to about 9, about 7 to about 8, about 8 to about 10, about 8 to about 9, or about 9 to about 10. In some embodiments, each molecule of the peptide composition comprises about 1 to about 8 peptide chains. In some embodiments, each molecule of the peptide composition comprises about one photosensitizer moiety and about 1 to about 8 peptide chains.

In some embodiments, the peptide chain of the charged peptide composition includes about 5 to about 40 amino acid residues. For example, the peptide chain can have about 5 to about 40 amino acid residues, such as about 5 to about 35, about 5 to about 30, about 5 to about 25, about 5 to about 20, about 5 to about 15, about 5 to about 10, about 7 to about 40, about 7 to about 35, about 7 to about 30, about 7 to about 25, about 7 to about 20, about 7 to about 15, about 7 to about 10, about 10 to about 40, about 10 to about 35, about 10 to about 30, about 10 to about 25, about 10 to about 20, about 10 to about 15, about 15 to about 40, about 15 to about 35, about 15 to about 30, about 15 to about 25, about 15 to about 20, about 20 to about 40, about 20 to about 35, about 20 to about 30, about 20 to about 25, about 25 to about 40, about 25 to about 35, about 25 to about 30, about 30 to about 40, about 30 to about 35, about 35 to about 40, or about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or about 40 amino acid residues. In some embodiments, the peptide chain comprises about 7 to about 40 amino acid residues. In some embodiments, the peptide chain comprises about 7 to about 20 amino acid residues. In some embodiments, the peptide chain comprises about 12 to about 15 amino acid residues. In some embodiments, the peptide chain comprises about 14 amino acid residues.

The methods and compositions provided herein can include amino acids or derivatives thereof. As used herein, an amino acid or derivative thereof refers to any amino acid, modified amino acid, natural amino acid, unnatural amino acid or amino acid analogue and the following twenty genetically encoded alpha-amino acids: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine. Derivatives of amino acids can be compounds that are synthesized amino acids. Derivatives of amino acids can include from 1 to 20 amino acid residues. Amino acids or derivatives thereof can also include, but are not limited to β- and γ-amino acid residues, D-amino acid residues, 6-aminohexanoic acid, 6-aminopentanoic acid, norleucine, norvaline, p-fluorophenylalanine, ethionine, phosphoserine, phosphothreonine, phosphotyrosine, hydroxyproline, γ-carboxyglutamate, hippuric acid, octahydroindole-2-carboxylic acid, statine, 1,2,3,4,-tetrahydroisoquinoline-3-carboxylic acid, penicillamine, ornithine, citrulline, β-alanine, α-methyl-alanine, para-benzoyl-phenylalanine, phenylglycine, propargylglycine, sarcosine, tert-butylglycine, TMG (trimethyl glycine/Betaine), L-taurine, L-carnitine, acetyl-L-carnitine, N-acetylcysteine and N,N-dimethyl glycine.

In some embodiments of the compositions and methods provided herein, the peptide composition is positively charged. In some embodiments, the peptide composition is positively charged and the liposomal composition is negatively charged. In some embodiments, the positively charged peptide composition includes peptides comprising amino acid residues with positive charges. In some embodiments, the positively charged peptide composition is enriched with amino acid residues with positive charges. In some embodiments, the positively charged peptide comprises arginine and other guanidinium-containing amino acid residues. In some embodiments, the peptide is enriched with a combination of arginine and other guanidinium-containing amino acid residues. In some embodiments, the positively charged peptide is enriched with arginine or other guanidinium-containing amino acid residues. In some embodiments, about 30% to about 50% of the amino acid residues of the positively charged peptide are arginine or other guanidinium-containing amino acid residue, such as about 30% to about 45%, about 30%, to about 40%, about 30% to about 35%, about 35% to about 50%, about 35% to about 45%, about 35% to about 40%, about 40% to about 50%, about 40% to about 45%, about 45% to about 50%, or about 30%, 31%, 32%, 33%, 34%, 35%, 36%, 37%, 38%, 39%, 40%, 41%, 42%, 43%, 44%, 45%, 46%, 47%, 48%, 49%, or about 50% of the amino acid residues of the positively charged peptide. In some embodiments, at least about 3 of the arginine or other guanidinium-containing amino acid residues of the positively charged peptide chain are on the same side of the alpha-helix, for example, about 3, 4, 5, 6, 7, 8, 9, or 10 of the arginine or other guanidinium-containing amino acid residues are on the same side of the alpha-helix. In some embodiments, about 30% to about 50% of the amino acid residues of the positively charged peptide are arginine or other guanidinium-containing amino acid residue and at least 3 are on the same side of the alpha-helix. In some embodiments, the peptide has the sequence RLARLARRLARLAR (SEQ ID NO:1). In some embodiments, the peptide has at least 90% sequence identity to the sequence RLARLARRLARLAR (SEQ ID NO:1).

In some embodiments, the peptide composition is positively charged and comprises a photosensitizer conjugated to a peptide chain that includes positively charged amino acid residues. In some embodiments, the photosensitizer is a hydrophobic photosensitizer. In some embodiments, the hydrophobic photosensitizer is zinc tetracarboxy phthalocyanine. In some embodiments, the peptide chain has a sequence corresponding to SEQ ID NO:1. In some embodiments, the peptide chain has at least 90% sequence identity to the sequence RLARLARRLARLAR (SEQ ID NO:1).

In some embodiments of the compositions and methods provided herein, the peptide composition is negatively charged. In some embodiments, the peptide composition is negatively charged and the liposomal composition is positively charged. In some embodiments, the negatively charged peptide composition includes peptides comprising amino acid residues with negative charges. In some embodiments, the negatively charged peptide comprises amino acid residues selected from among aspartic acid and derivatives thereof, glutamic acid and derivatives thereof, and amino acid residues comprising dicarboxylic acid or tricarboxylic acid side chains. In some embodiments, the negatively charged peptide comprises amino acid residues comprising dicarboxylic acid or tricarboxylic acid side chains. In some embodiments, the peptide has an amino acid sequence that includes 2-amino-4-carboxy-pentanedioic acid.

In some embodiments, about 40% to about 100% of the amino acid residues of the negatively charged peptide are amino acid residues comprising dicarboxylic acid or tricarboxylic acid side chains, such as about 40% to about 90%, about 40% to about 80%, about 40% to about 70%, about 40% to about 60%, about 40% to about 50%, about 50% to about 100%, about 50% to about 90%, about 50% to about 80%, about 50% to about 70%, about 50% to about 60%, about 60% to about 100%, about 60% to about 90%, about 60% to about 80%, about 60% to about 70%, about 70% to about 100%, about 70% to about 90%, about 70% to about 80%, about 80% to about 100%, about 80% to about 90%, about 90% to about 100%, or about 40%, 45%, 50%, 55%, 60%, 65%, 70%, 75%, 80%, 85%, 90%, 95%, 96%, 97%, 98%, 99%, or about 100% of the amino acid residues of the negatively charged peptide. In some embodiments, about 40% to about 100% of the amino acid residues of the negatively charged peptide are amino acid residues comprising dicarboxylic acid or tricarboxylic acid side chains. In some embodiments, about 40% to about 100% of the amino acid residues of the negatively charged peptide are 2-amino-4-carboxy-pentanedioic acid.

In some embodiments, the peptide composition is negatively charged and comprises a photosensitizer conjugated to a peptide chain that includes negatively charged amino acid residues. In some embodiments, the photosensitizer is a hydrophilic photosensitizer. In some embodiments, the peptide chain includes 2-amino-4-carboxy-pentanedioic acid.

In some embodiments, the charged peptide composition further includes a targeting moiety. The term "targeting moiety" as used herein refers to any molecular structure which assists a compound or other molecule in binding or otherwise localizing to a particular target, a target area, entering target cell(s), or binding to a target receptor. For example, targeting moieties can include, but are not limited to, peptides, proteins, including antibodies and protein fragments capable of binding to a desired target site in vivo or in vitro, small molecules, anticancer agents, polynucleotide-binding agents, carbohydrates, ligands for cell surface receptors, aptamers, lipids (including cationic, neutral, and steroidal lipids, virosomes, and liposomes), antibodies, and hormones.

In some embodiments, the targeting moiety is a peptide chain. In some embodiments, the peptide chain targeting moiety includes about 5 to about 20 amino acid residues. For example, the peptide chain targeting moiety can have about 5 to about 20 amino acid residues, such as about 5 to about 15, about 5 to about 10, about 7 to about 20, about 7 to about 15, about 7 to about 10, about 10 to about 20, about 10 to about 15, about 15 to about 20, or about 5, 6, 7, 8, 9, 10, 11, 12, 13, 14, 15, 16, 17, 18, 19, or about 20 amino acid residues. In some embodiments, the peptide chain targeting moiety comprises about 4 to about 20 amino acid residues. In some embodiments, the peptide chain targeting moiety comprises about 7 to about 20 amino acid residues. In some embodiments, the peptide chain targeting moiety includes, but is not limited to, sequences such as Ala-Glu-Tyr-Leu-Arg (SEQ ID NO:2), Tyr-Glu-Val-His-Thr-Tyr-Tyr-Leu-Asp (SEQ ID NO:3), Tyr-Val-Met-Gly-His-Phe-Arg-Trp-Asp-Arg-Phe (SEQ ID NO:4), Arg-Gly-Asp motif sequences, and Cys-Ser-Lys-Cys (SEQ ID NO: 5) motif sequences.

In some embodiments, the targeting moieties is useful for delivery of the peptide composition to specific cell types, as well as sub-cellular locations. In some embodiments, the targeting moiety is able to bind to cell surface receptors on the target tissue or organ. Useful targeting moieties include, but are not limited to, those that target cell surface receptors overexpressed on cancer cells, the epidermal growth factor receptor, epithelial cell adhesion molecule, integrins, insulin-like growth factor receptor IGF1R, or melanocortin receptors. In some embodiments, the cell surface receptors are overexpressed on cancer cells.

In some embodiments, the targeting moiety is bound to the peptide chain. In some embodiments, the targeting moiety is bound to the peptide chain at the end of the peptide chain opposite of where the photosensitizer is bound.

Administration of the Compositions

As used herein, the term "administration" or "administering" refers to a method of giving a dosage of a compound or composition described herein to a subject. "Subject," as used herein, means a human or a non-human mammal, e.g., a dog, a cat, a mouse, a rat, a cow, a sheep, a pig, a goat, a non-human primate or a bird, e.g., a chicken, as well as any other vertebrate or invertebrate. In some embodiments, the subject is a human. In some embodiments, the method of administration is, e.g., orally, subcutaneously, intravenously, intranasally, topically, transdermally, intraperitoneally, intramuscularly, intrapulmonarilly, vaginally, rectally, ontologically, neuro-otologically, intraocularly, subconjuctivally, via anterior eye chamber injection, intravitreally, intraperitoneally, intrathecally, intracystically, intrapleurally, via wound irrigation, intrabuccally, intra-abdominally, intra-articularly, intra-aurally, intrabronchially, intracapsularly, intrameningeally, via inhalation, via endotracheal or endobronchial instillation, via direct instillation into pulmonary cavities, intraspinally, intrasynovially, intrathoracically, via thoracostomy irrigation, epidurally, intratympanically, intracisternally, intravascularly, intraventricularly, intraosseously, via irrigation of infected bone, or via application as part of any admixture with a prosthetic device. The preferred method of administration can vary depending on various factors, e.g., the components of the composition, the site of the disease, target tissue, or target organ, the disease involved, and the severity of the disease. In some embodiments of the methods provided herein, administration is intravenous. In some embodiments of the methods provided herein, administration is via injection.

In some embodiments of the methods described herein, the liposomal composition (total lipids) and the peptide composition are administered to the subject at a molar ratio of about 40:1 to about 1:5, such as about 1:80 to about 1:70, about 1:80 to about 1:60, about 1:80 to about 1:50, about 1:80 to about 1:40, about 1:80 to about 1:30, about 1:80 to about 1:20, about 1:80 to about 1:10, about 1:80 to about 1:5, about 1:70 to about 1:60, about 1:70 to about 1:50, about 1:70 to about 1:40, about 1:70 to about 1:30, about 1:70 to about 1:20, about 1:70 to about 1:10, about 1:70 to about 1:5, about 1:60 to about 1:50, about 1:60 to about 1:40, about 1:60 to about 1:30, about 1:60 to about 1:20, about 1:60 to about 1:10, about 1:60 to about 1:5, about 1:50 to about 1:40, about 1:50 to about 1:30, about 1:50 to about 1:20, about 1:50 to about 1:10, about 1:50 to about 1:5, about 1:40 to about 1:30, about 1:40 to about 1:20, about 1:40 to about 1:10, about 1:40 to about 1:5, about 1:30 to about 1:20, about 1:30 to about 1:10, about 1:30 to about 1:5, about 1:20 to about 1:10, about 1:20 to about 1:5, about 1:10 to about 1:5, or about 1:80, 1:70, 1:60, 1:50, 1:40, 1:30, 1:20, 1:10, or about 1:5. In some embodiments, the molar ratio of liposomal composition (total lipids) to peptide-photosensitizer conjugate administered is about 1:20. In some embodiments, the molar ratio of liposomal composition (total lipids) to peptide-photosensitizer conjugate administered is about 1:10.

In some embodiments of the methods described herein, the liposomal composition and the peptide composition are administered to the subject at a ratio of about 40:1 to about 1:1 by weight, such as about 35:1 to about 1:1, about 30:1 to about 1:1, about 25:1 to about 1:1, about 20:1 to about 1:1, about 15:1 to about 1:1, about 10:1 to about 1:1, about 5:1 to about 1:1, about 2:1 to about 1:1, about 40:1 to about 2:1, about 35:1 to about 2:1, about 30:1 to about 2:1, about 25:1 to about 2:1, about 20:1 to about 2:1, about 15:1 to about 2:1, about 10:1 to about 2:1, about 5:1 to about 2:1, about 40:1 to about 5:1, about 35:1 to about 5:1, about 30:1 to about 5:1, about 25:1 to about 5:1, about 20:1 to about 5:1, about 15:1 to about 5:1, about 10:1 to about 5:1, about 40:1 to about 10:1, about 35:1 to about 10:1, about 30:1 to about 10:1, about 25:1 to about 10:1, about 20:1 to about 10:1, about 15:1 to about 10:1, about 40:1 to about 15:1, about 35;1 to about 15:1, about 30:1 to about 15:1, about 25:1 to about 15:1, about 20:1 to about 15:1, about 40:1 to about 20:1, about 35:1 to about 20:1, about 30:1 to about 20:1, about 25:1 to about 20:1, or about 40:1 to about 35:1 by weight, or about 40:1, 35:1, 30:1, 25:1, 20:1, 15:1, 10:1, 5:1, 2:1, or about 1:1 by weight. In some embodiments, the liposomal composition and the peptide composition are administered to the subject at a ratio of about 40:1 to about 1:1 by weight, according to the dry (lyophilized) weight of both compositions.

In some embodiments of the methods provided herein, the liposomal composition and the peptide composition are administered simultaneously. In some embodiments, the liposomal composition and the peptide composition are administered separately. In some embodiments, when the liposomal composition and the peptide composition are administered separately, the second composition is administered immediately after administration of the first composition. In some embodiments, the second composition is administered up to about 24 hours after administration of the first composition, for example, the second composition is administered about 1, 2, 3, 4, 5, 6, 8, 10, 12, 15, 20, or about 24 hours after administration of the first composition. In some embodiments, the second composition is administered about 1 to about 24 hours after administration of the first composition, such as about 1 hour to about 20 hours, about 1 hour to about 15 hours, about 1 hour to about 12 hours, about 1 hour to about 10 hours, about 1 hour to about 8 hours, about 1 hour to about 6 hours, about 1 hour to about 5 hours, about 1 hour to about 4 hours, about 1 hour to about 3 hours, about 1 hour to about 2 hours, about 2 hours to about 20 hours, about 2 hours to about 15 hours, about 2 hours to about 12 hours, about 2 hours to about 10 hours, about 2 hours to about 8 hours, about 2 hours to about 6 hours, about 2 hours to about 5 hours, about 2 hours to about 4 hours, about 2 hours to about 3 hours, about 3 hours to about 20 hours, about 3 hours to about 15 hours, about 3 hours to about 12 hours, about 3 hours to about 10 hours, about 3 hours to about 8 hours, about 3 hours to about 6 hours, about 3 hours to about 5 hours, about 3 hours to about 4 hours, about 4 hours to about 20 hours, about 4 hours to about 15 hours, about 4 hours to about 12 hours, about 4 hours to about 10 hours, about 4 hours to about 8 hours, about 4 hours to about 6 hours, about 4 hours to about 5 hours, about 5 hours to about 20 hours, about 5 hours to about 15 hours, about 5 hours to about 12 hours, about 5 hours to about 10 hours, about 5 hours to about 8 hours, about 5 hours to about 6 hours, about 6 hours to about 20 hours, about 6 hours to about 15 hours, about 6 hours to about 12 hours, about 6 hours to about 10 hours, about 6 hours to about 8 hours, about 8 hours to about 20 hours, about 8 hours to about 15 hours, about 8 hours to about 12 hours, about 8 hours to about 10 hours, about 10 hours to about 20 hours, about 10 hours to about 15 hours, about 10 hours to about 12 hours, about 12 hours to about 20 hours, about 12 hours to about 15 hours, or about 15 hours to about 20 hours after administration of the first composition.

In some embodiments, the liposomal composition is administered before the peptide composition is administered. In some embodiments, the peptide composition is administered before the liposomal composition is administered. In some embodiments, the liposomal composition is administered about 1 hour to about 6 hours before the peptide composition is administered. In some embodiments, the liposomal composition is administered about 3 hours to about 5 hours before the peptide composition is administered.

In some embodiments of the methods described herein, the liposomal composition accumulates at the target tissue or organ after administration. In some embodiments, the target tissue or organ is a tumor. In some embodiments, accumulation is enhanced at the tumor because of the enhanced permeability and retention (EPR) effect. In some embodiments, the desired amount of liposomal composition accumulation occurs at the tumor about 3 hour to about 5 hours after administration.

In some embodiments of the methods described herein, the peptide composition accumulates at the target tissue or organ after administration. In some embodiments, the target tissue or organ is a tumor. In some embodiments, the peptide composition comprises a targeting moiety that targets a tumor.

In some embodiments of the methods described herein, after administration of the charged liposomal composition and the oppositely charged peptide composition, a noncovalent association is formed between the liposomal composition and the peptide composition. In some embodiments, the noncovalent association is an electrostatic interaction, or electrostatic bond, between the liposomal composition and peptide composition. In some embodiments, the noncovalent association is formed at the target tissue or organ.

Illumination-Induced Small Molecule Release

The methods provided herein allow for externally controlled release of the small molecule from the liposome. In the methods provided herein, the methods include applying low intensity light to induce release of the small molecule from the liposome after administration of the liposomal composition and the peptide composition. In some embodiments, the drug is permeabilized into the target tissue or organ after release from the liposome. For example, the methods described herein provide efficient release of the small molecule, e.g., diagnostic, imaging, or therapeutic agent, upon illumination of the interacting liposomes and photosensitizer-peptide conjugate. In some embodiments, this avoids provocation of drug resistance by sub-therapeutic rate of drug release and allows targeting of enhanced release by local application of external stimulus with lower light intensity and dose than required for a photodynamic effect.

The suitable wavelength, or range of wavelengths, used for illumination will depend on the particular photosensitizer(s) used. Wavelength specificity for photoactivation depends on the molecular structure of the photosensitizer. Determination of suitable wavelength, light intensity, and duration of illumination is within ordinary skill in the art. The intensity must be sufficient for the light to reach the target tissue. The duration must be sufficient to photoactivate enough photosensitizing compound to act on the target tissue. In some embodiments, the provided methods allow enhanced release of the small molecule at the target tissue or organ by application of external illumination with lower light intensity and dose than required for photodynamic therapy. In some embodiments, the same extent of small molecule release from the liposome, for example, about 50%, is achieved by using less light intensity and shorter duration of illumination as compared to illumination with higher intensity light and/or longer duration.

In some embodiments, the intensity of the low intensity light is from about 10 $mW/cm^2$ to about 200 $mW/cm^2$. For example, the intensity of the light is from about 10 $mW/cm^2$ to about 175 $mW/cm^2$, or about 10 $mW/cm^2$ to about 150 $mW/cm^2$, or about 10 $mW/cm^2$ to about 125 $mW/cm^2$, or about 10 $mW/cm^2$ to about 100 $mW/cm^2$, or about 10 $mW/cm^2$ to about 75 $mW/cm^2$, or about 10 $mW/cm^2$ to about 50 $mW/cm^2$, or about 10 $mW/cm^2$ to about 30 $mW/cm^2$, or about 30 $mW/cm^2$ to about 200 $mW/cm^2$, or about 30 $mW/cm^2$ to about 175 $mW/cm^2$, or about 30 $mW/cm^2$ to about 150 $mW/cm^2$, or about 30 $mW/cm^2$ to about 125 $mW/cm^2$, or about 30 $mW/cm^2$ to about 100 $mW/cm^2$, or about 30 $mW/cm^2$ to about 75 $mW/cm^2$, or about 30 $mW/cm^2$ to about 50 $mW/cm^2$, or about 50 $mW/cm^2$ to about 200 $mW/cm^2$, or about 50 $mW/cm^2$ to about 175 $mW/cm^2$, or about 50 $mW/cm^2$ to about 150 $mW/cm^2$, or about 50 $mW/cm^2$ to about 125 $mW/cm^2$, or about 50 $mW/cm^2$ to about 100 $mW/cm^2$, or about 50 $mW/cm^2$ to about 75 $mW/cm^2$, or about 75 $mW/cm^2$ to about 200 $mW/cm^2$, or about 75 $mW/cm^2$ to about 175 $mW/cm^2$, or about 75 $mW/cm^2$ to about 150 $mW/cm^2$, or about 75 $mW/cm^2$ to about 125 $mW/cm^2$, or about 75 $mW/cm^2$ to about 100 $mW/cm^2$, or about 100 $mW/cm^2$ to about 200 $mW/cm^2$, or about 100 $mW/cm^2$ to about 175 $mW/cm^2$, or about 100 $mW/cm^2$ to about 150 $mW/cm^2$, or about 100 $mW/cm^2$ to about 125 $mW/cm^2$, or about 125 $mW/cm^2$ to about 200 $mW/cm^2$, or about 125 $mW/cm^2$ to about 175 $mW/cm^2$, or about 125 $mW/cm^2$ to about 150 $mW/cm^2$, or about 150 $mW/cm^2$ to about 200 $mW/cm^2$, or about 150 $mW/cm^2$ to about 175 $mW/cm^2$, or about 175 $mW/cm^2$ to about 200 $mW/cm^2$. In some embodiments, the intensity of the light is less than about 200 $mW/cm^2$. In some embodiments, the intensity of the light is less than about 100 $mW/cm^2$. In some embodiments, the intensity of the light is less than about 50 $mW/cm^2$. In some embodiments, the intensity of the light is about 30-40 $mW/cm^2$. In some embodiments, the intensity of the light is about 10 $mW/cm^2$. In some embodiments, the intensity of the light is about 20 $mW/cm^2$. In some embodiments, the intensity of the light is about 40 $mW/cm^2$.

Figure 2B:
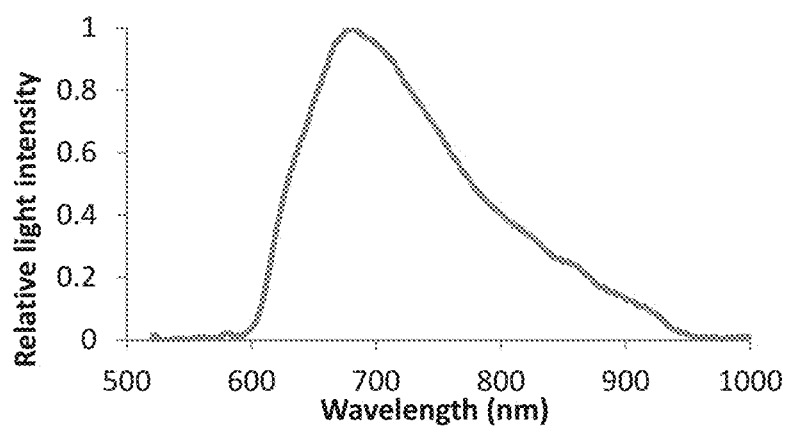

In some embodiments, the light source is a halogen lamp. In some embodiments, the light source is a halogen lamp coupled with a flowing water filter to remove the thermal radiation. In some embodiments, the halogen lamp is coupled with a flowing water filter to remove the thermal radiation and a red optical filter (FIGS. 1A-1B). In some embodiments, the final illumination is provided in a wide band of about 600 nm to about 950 nm with a maximum at about 650 nm to 700 nm, such as about 680 nm (FIG. 2B). In other embodiments, the light source is a continuous range (white) lamp with adjustable wavelength optical filter. In some embodiments, the light source is based on a light emitting diode (LED) or a laser diode. In some embodiments, the LED or laser diode has a maximum of emission that is chosen according to the wavelength of a maximum optical absorption of the photosensitizer. For example, wavelengths such as about 662 nm for chlorin-e6 derivatives; about 675 nm, about 680 nm, about 690 nm, about 720 nm, or about 730 nm for some phthalocyanine derivatives; about 762 nm to about 805 nm for some bacteriochlorin or bacteriopheophorbide derivatives; or any other available narrowband light sources within the range of about 660 nm to 860 nm.

In some embodiments of the methods provided herein, the target tissue is a tumor. In the methods provided herein, application of the low intensity light does not substantially damage tissue or organs other than the target tissue or organ. In some embodiments, the application of the low intensity light does not substantially damage the tissues or organs surrounding the tumor or tissues or organs that lay between the target tissue or organ and the illuminated area. In some embodiments, application of the low intensity light does not cause any damage to the tissues or organs surrounding the target tissue or organ, such as a tumor. Examples of the tissue damage that can be avoided by using induction of drug release by low intensity light include, but are not limited to, burn damage of skin (for transcutaneous illumination of subcutaneous tumors); damage of skin, muscle layer, and other respective tissue (for the treatment of large sized or deep-seated tumors); mucosal layer damage (for transmucosal illumination of inner organ tumor); damage to the vitreous body of an eye (for transvitreal illumination of retinal and uveal tumors); and others.

In some embodiments, the low intensity light is applied up to about 24 hours after both compositions have been administered, for example, the low intensity light is applied about 1, 2, 3, 4, 5, 6, 8, 10, 12, 15, 20, or about 24 hours after both compositions have been administered. In some embodiments, the low intensity light is applied about 1 to about 24 hours after both compositions have been administered, such as about 1 hour to about 20 hours, about 1 hour to about 15 hours, about 1 hour to about 12 hours, about 1 hour to about 10 hours, about 1 hour to about 8 hours, about 1 hour to about 6 hours, about 1 hour to about 5 hours, about 1 hour to about 4 hours, about 1 hour to about 3 hours, about 1 hour to about 2 hours, about 2 hours to about 20 hours, about 2 hours to about 15 hours, about 2 hours to about 12 hours, about 2 hours to about 10 hours, about 2 hours to about 8 hours, about 2 hours to about 6 hours, about 2 hours to about 5 hours, about 2 hours to about 4 hours, about 2 hours to about 3 hours, about 3 hours to about 20 hours, about 3 hours to about 15 hours, about 3 hours to about 12 hours, about 3 hours to about 10 hours, about 3 hours to about 8 hours, about 3 hours to about 6 hours, about 3 hours to about 5 hours, about 3 hours to about 4 hours, about 4 hours to about 20 hours, about 4 hours to about 15 hours, about 4 hours to about 12 hours, about 4 hours to about 10 hours, about 4 hours to about 8 hours, about 4 hours to about 6 hours, about 4 hours to about 5 hours, about 5 hours to about 20 hours, about 5 hours to about 15 hours, about 5 hours to about 12 hours, about 5 hours to about 10 hours, about 5 hours to about 8 hours, about 5 hours to about 6 hours, about 6 hours to about 20 hours, about 6 hours to about 15 hours, about 6 hours to about 12 hours, about 6 hours to about 10 hours, about 6 hours to about 8 hours, about 8 hours to about 20 hours, about 8 hours to about 15 hours, about 8 hours to about 12 hours, about 8 hours to about 10 hours, about 10 hours to about 20 hours, about 10 hours to about 15 hours, about 10 hours to about 12 hours, about 12 hours to about 20 hours, about 12 hours to about 15 hours, or about 15 hours to about 20 hours after both compositions have been administered.

Storage of the Compositions

In the methods provided herein, the charged liposomal composition and the charged peptide composition are stored separately prior to administration. For example, the liposomal composition that includes the small molecule is stored separately from the peptide composition that contains the photosensitizer. Thus, the methods provided herein avoid the unintentional release of the small molecule from the liposome prior to administration, for example, as a result of oxidation of lipids that disrupt the stability of the liposomal lipid membrane.

In some embodiments, the liposomal composition and the peptide composition are stored in lyophilized form. In some embodiments, the liposomal composition is stored in lyophilized form and further includes an antioxidant. Typically, the storage stability of liposomes and liposomal compositions is decreased by oxidation of the lipids of the lipid membrane over the course of storage. Lipophilic antioxidants, such as tocopherol and its derivatives, have traditionally been used to inhibit background oxidation of lipids. However, such antioxidants cannot be used in liposomal compositions that also include a photosensitizer, as the antioxidant will conflict with the intentional oxidation of the administered liposomes, which is required for release of the small molecule. By contrast, in some embodiments, the liposomal compositions provided herein include an antioxidant. In some embodiments, the liposomal compositions provided herein include a hydrophilic antioxidant. In some embodiments, the antioxidant protects the liposomes from oxidation during storage, such as storage in lyophilized form, and does not significantly inhibit the release of the small molecule from the liposome when co-illuminated with a photosensitizer.

In some embodiments, the antioxidant is a hydrophilic antioxidant, such as a nontoxic hydrophilic antioxidant. Examples of hydrophilic antioxidants include, but are not limited to, histidine, histidine derivatives, the reduced form of glutathione, sodium thiosulfate, and mixtures thereof. Additional hydrophilic antioxidants include ascorbic acid, sodium ascorbate, cysteine, glutathione, dihydrolipoic acid, 2-mercaptoethane sulfonic acid, 2-mercaptobenzimidazole sulfonic acid, 6-hydroxy-2,5,7,8-tetramethylchroman-2-carboxylic acid, sodium metabi sulfite, salts thereof, and mixtures thereof. In some embodiments, the hydrophilic antioxidant is selected from among histidine, histidine derivatives, ascorbic acid, sodium ascorbate, the reduced form of glutathione, and sodium thiosulfate. In some embodiments, the hydrophilic antioxidant is L-histidine free base. In some embodiments, the hydrophilic antioxidant is L-histidine HCl. In some embodiments, the hydrophilic antioxidant is the reduced from of glutathione (reduced GSH). In some embodiments, the hydrophilic antioxidant is sodium thiosulfate.

In some embodiments, the antioxidant is present in an amount sufficient to prevent, inhibit, or reduce the degradation of the liposomes present in the liposomal composition, such as in a lyophilized liposomal composition. For example, the antioxidant can be present at a concentration of at least about or about 0.1 mM, 0.5 mM, 1 mM, 10 mM, 50 mM, 100 mM, 250 mM, 500 mM, 1 M, 2 M, or 5M, or from about 0.1 mM to about 1 M, from about 0.1 mM to about 500 mM, from about 0.1 mM to about 250 mM, from about 0.1 mM to about 100 mM, or from about 1 mM to about 50 mM.

Kits

Also provided herein are kits, for example, drug delivery kits. Typically, a kit includes one or more compositions as described herein, e.g., a charged liposomal composition that includes a liposome and a drug encapsulated by the liposome and an oppositely charged peptide composition that includes a peptide chain conjugated to a photosensitizer. In some embodiments, the liposomal composition and the peptide composition in the kit are stored separately prior to administration to a subject in need thereof. In certain embodiments, a kit can include one or more delivery systems, e.g., for delivering or administering the compositions as provided herein, and directions for use of the kit (e.g., instructions for treating a subject). In some embodiments, the kit can include a composition as described herein and a label that indicates that the contents are to be administered to a patient with cancer. The actual dose of the compositions provided herein depends on the specific composition, and on the condition to be treated; the selection of the appropriate dose is well within the knowledge of the skilled artisan.

Methods for Delivering a Small Molecule to a Target Tissue or Organ

Thus, provided herein are methods for delivering a small molecule to a target tissue or organ of a subject in need thereof. The method comprises: a) administering a charged liposomal composition comprising a liposome and a small molecule encapsulated by the liposome; b) administering a charged peptide composition comprising a peptide chain conjugated to a photosensitizer; and c) applying low intensity light to induce release of the small molecule from the liposome and permeabilization of the small molecule at the target tissue or organ; wherein the liposomal composition and peptide composition are oppositely charged.

In some embodiments, the method comprises a) administering a negatively charged liposomal composition that contains a liposome comprising anionic phospholipids and a hydrophilic small molecule encapsulated by the liposome; b) administering a positively charged peptide composition comprising a peptide chain with at least 90% sequence identity to the sequence RLARLARRLARLAR (SEQ ID NO:1) conjugated to a photosensitizer; and c) applying low intensity light to induce release of the small molecule from the liposome. In some embodiments, the hydrophilic small molecule is a chemotherapeutic agent. In some embodiments, the hydrophilic small molecule is a fluorescent marker. In some embodiments, the photosensitizer is a phthalocyanine compound. In some embodiments, the liposomal composition and the peptide composition are stored separately prior to administration.

In some embodiments, the method comprises a) administering a positively charged liposomal composition that includes a liposome comprising cationic phospholipids and a hydrophobic small molecule encapsulated by the liposome; b) administering a negatively charged peptide composition comprising a peptide chain that contains negatively charged amino acid residues conjugated to a photosensitizer; and c) applying low intensity light to induce release of the small molecule from the liposome. In some embodiments, the liposomal composition and the peptide composition are stored separately prior to administration.

Unless otherwise defined, all technical and scientific terms used herein have the same meaning as commonly understood by one of ordinary skill in the art to which this disclosure belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

EXAMPLES

The light-induced drug release from liposomes was shown in a number of experiments with liposomes loaded with the fluorescent marker calcein or chemotherapeutic compound doxorubicin hydrochloride, using a conjugate of a synthesized peptide of the sequence RLARLARRLAR-LAR (SEQ ID NO:1) (where letters R, L and A denote respectively residues of arginine, leucine and alanine) and the photosensitizer zinc tetra-carboxyphthalocyanine (provided by scientific center NIOPIK (Russia)).

Studies included preparation of a positively-charged photosensitizer-peptide conjugate, preparation of fluorescent marker- or drug-loaded negatively charged liposomes, studies of the release of liposome-encapsulated marker upon illumination under different conditions in comparison to controls, study of enhancement of biological action of illuminated liposome-encapsulated chemotherapeutic compound, as well as studies of the inhibition of marker release by antioxidants of different hydrophilicity, as described in the following examples.

Example 1: Peptide Synthesis and Conjugation with Photosensitizer

General Procedure:

Peptide synthesis was performed on a 0.1 mmol scale (by amine groups equivalents) on Rink amide resin in a 15-25 mL manual reaction vessel. Assembly was made by an Fmoc-chemistry approach utilizing amino acid derivatives with α-amino groups protected by the fluorenylmethoxycarbonyl (Fmoc) group, and reactive side chains protected as follows: Arg with 2,2,4,6,7-pentamethyldihydro-benzofuran-5-sulfonyl (Pbf), Asn, Gln, His and Cys—with trityl, Asp, Glu, Thr, Ser—with t-butyl, Lys and Trp—with t-butyloxycarbonyl (Boc).

Peptide assembly was performed as follows. (i) Particles of Rink amide resin were pre-swelled with dimethylformamide (DMF) for 30 minutes. (ii) Fmoc protective groups were removed with 20% piperidine in DMF (1×5 min and 1×15 min). (iii) The Fmoc-amino acid derivative (0.4 mmol) was dissolved in a 0.38 M solution of HBTU in DMF (1 mL, 0.38 mmol); reagents were activated for coupling by adding diisopropylethylamine (DIEA; 105 µL, 0.6 mmol) for 2 minutes with occasional vortexing. (iv) Particles were washed with DMF (45 s continuous flow wash) and drained to the level of the particles. (v) The activated amino acid derivative solution was transferred to the reaction vessel and rocked on a wrist-arm shaker or sparged with bubbling nitrogen for 4 hours. (vi) The coupling solution was drained from the reaction vessel, and the particles were washed with DMF (45 s continuous flow wash), after which a 5 mg sample of particles was removed to determine the coupling yield by the quantitative ninhydrin test. (vi) Fmoc protective groups were removed with 20% piperidine in DMF (1×5 min and 1×15 min). (viii) Steps (iii) to (vii) were repeated until the sequence of the desired peptide was assembled. (ix) The carboxylated photosensitizer moiety was coupled to the N-terminus of the assembled peptide in the same manner as the amino acid derivatives, according to steps (iii) to (vi) of the above description. (x) The resin particles with protected assembled peptide or its conjugate with photosensitizer were washed with DCM (45 s continuous flow wash), then subjected to simultaneous deprotection of the acid labile side chain-protecting groups and cleavage of peptide from the resin by 3 hours treatment with a mixture of trifluoroacetic acid (TFA), triisopropylsilane and water (95/2.5/2.5, v/v/v).

The cleaved peptide was precipitated from the TFA solution by ice-cold anhydrous diethyl ether, washed by cold diethyl ether from the residual acid and freeze-dried for further use.

To characterize the peptide product, a sample was redissolved in 3% aqueous acetonitrile and separated to fractions by reverse-phase HPLC. The elution was provided by the mobile phase mixed from two individual buffers, A (0.1% vol. TFA in water) and B (60% vol. acetonitrile and 0.09% vol. TFA in water) by programmed gradient. The main fraction was identified by MALDI-TOF method.

Figure 3:
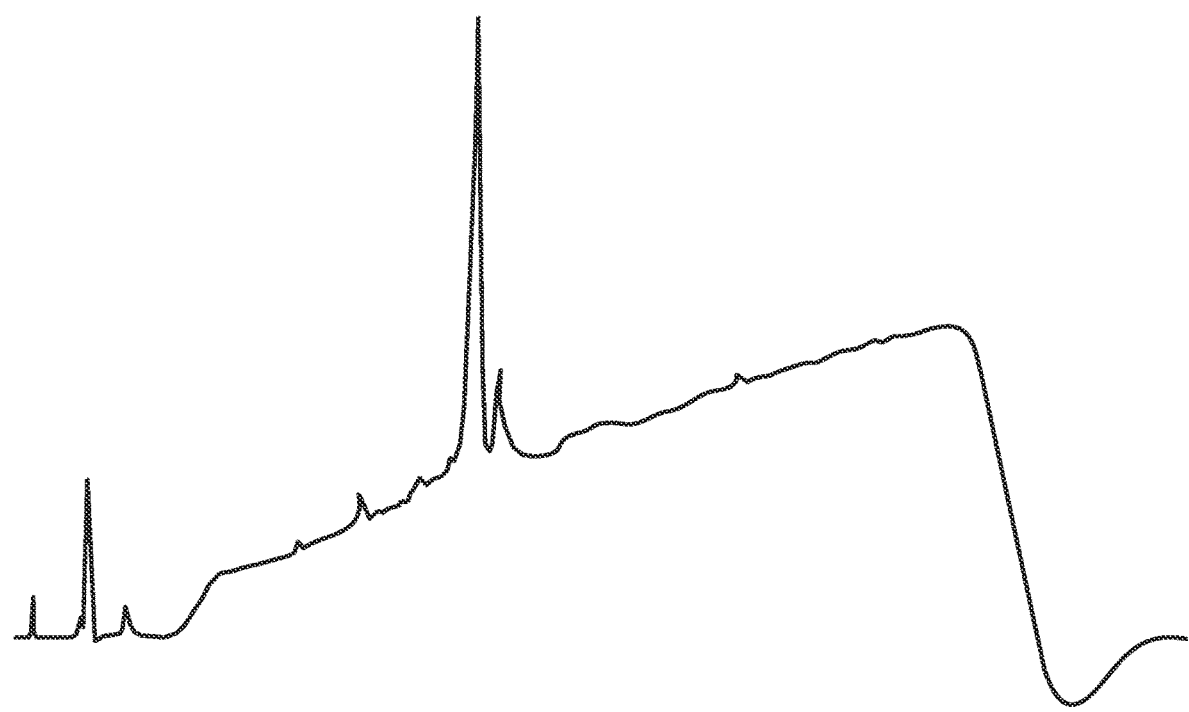
FIG. 3 is the analytical HPLC trace of the RLARLARRLARLAR peptide (SEQ ID NO:1).
Figure 4A:
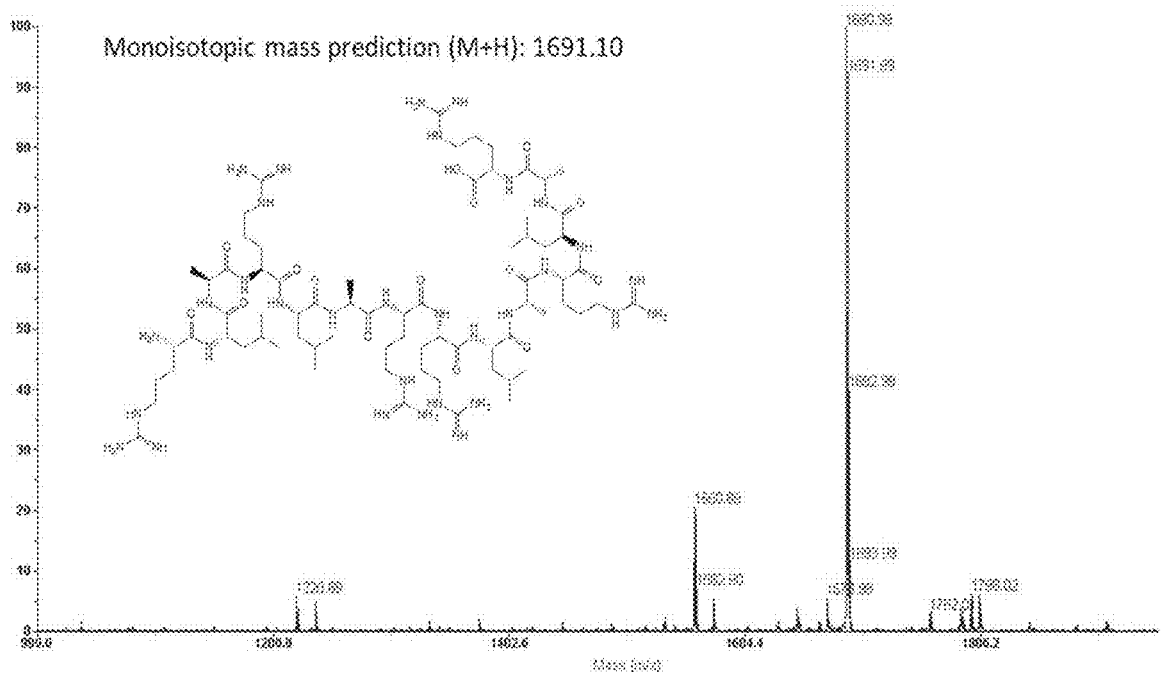
FIGS. 4A-4B are MALDI-TOF mass spectra of the RLARLARRLARLAR peptide (SEQ ID NO:1) (FIG. 4A) and its conjugate with the photosensitizer (FIG. 4B).
Figure 4B:
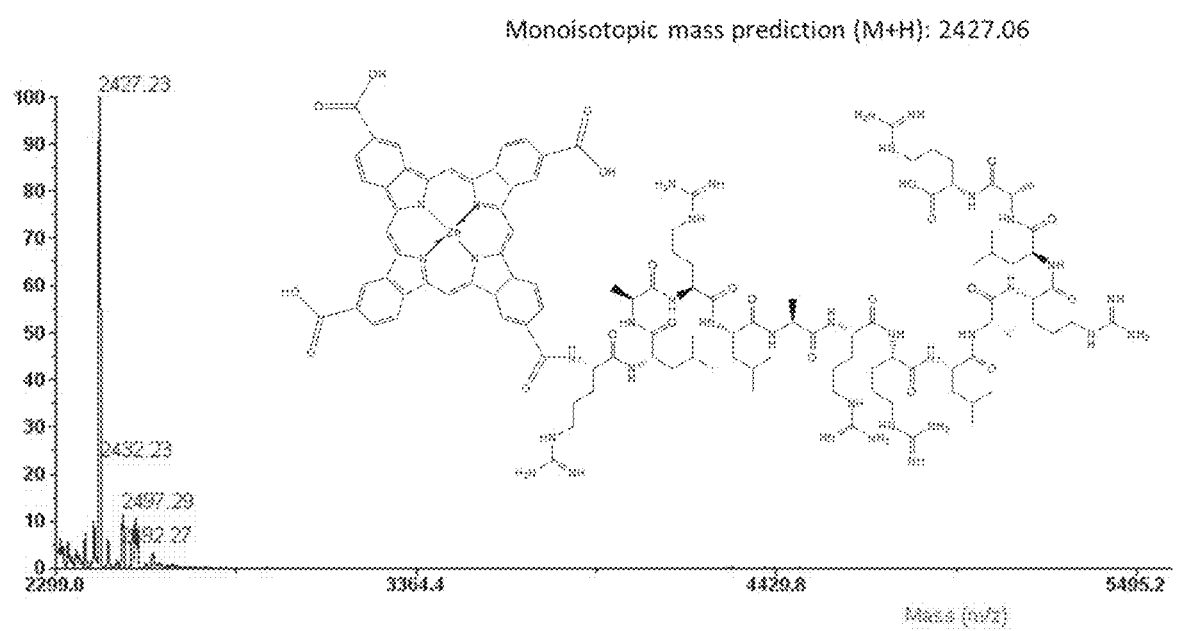

RLARLARRLARLAR Peptide-Photosensitizer Conjugate:

Synthesis and assembly of a peptide with the sequence RLARLARRLARLAR (SEQ ID NO:1) and conjugation with the photosensitizer zinc tetracarboxyphthalocyanine was performed according to the general procedure described above. HPLC of the peptide product with a linear gradient of 3 to 60% of acetonitrile in the mobile phase over 45 min showed 79% homogeneity of synthesis of the main product (FIG. 3). Mass-spectroscopy of the main product by MALDI-TOF technique showed the main m/z values for the peptide and photosensitizer-peptide conjugate of 1691 and 2427, respectively, corresponding to theoretically predicted values (FIGS. 4A-4B).

Example 2: Preparation and Characterization of Liposomes

Liposomes were prepared from 1-stearoyl-2-oleoyl-sn-glycero-3-phosphocholine, 1-stearoyl-2-oleoyl-sn-glycero-3-phosphoserine (providing the negative charge on liposomes) and cholesterol, using the technique of hydration of lipis film. Liposomes were loaded with either a fluorescent marker (calcein) or a drug (doxorubicin hydrochloride) to study the release using either a passive or active loading approach, respectively.

Passive loading (used for the fluorescent marker calcein): Lipid films were prepared by drying from mixed solutions of phospholipids and cholesterol in chloroform using flow of filtered nitrogen gas and eliminating residual solvent by freeze-drying. Crude liposomes (large multilamellar vesicles) were obtained by hydrating films with 60 mM solution of calcein in 0.1 M sodium phosphate buffer pH 7.4. Crude liposomes were processed to unilamellar vesicles using freeze-thaw technique and separated from non-entrapped calcein in the supernatant by gel filtration on a Sephadex G15 column.

Active loading (used for the drug doxorubicin hydrochloride): Lipid films were prepared as described above, hydrated with 0.25 M ammonium citrate and processed to unilamellar vesicles by freeze-thawing. Blank liposomes were then co-incubated with a 3 mg/mL solution of doxorubicin hydrochloride in HEPES buffer (pH 8.2-8.4), causing the doxorubicin to load into liposomes by pH gradient and remain there by forming a gel-like structure.

Example 3: Induction of Release of Liposomal Load by External Physical Stimulus

Studies were performed on the fluorescent marker- or drug-loaded liposomes described above diluted to a concentration of 0.2 mM by total lipids with or without the photosensitizer-peptide conjugate described above at 1:80 to 1:5 molar ratio to total lipids. Optionally, samples were also supplied with antioxidants/reducing agents or other additional substances at different concentrations. Samples were either illuminated as described below or kept for the same time period under different control conditions.

Illumination of prepared liposomes with or without photosensitizer-peptide conjugate was mostly preformed using a setup that included a halogen utility lamp, a 2-inch thick flowing water filter to cut infrared irradiation above 950 nm and a red optical cast plastic filter (EdmundOptics) to cut off light irradiation below 620 nm (FIG. 1). Resulting transmitted light was of a relatively wide spectrum (620-950 nm) and a power density up to 40 $mW/cm^2$ at the level of samples. A decrease of power density for the parametric studies was achieved by increasing the height of the halogen source above the water filter. The incident light spectrum was several times wider than the absorption spectrum of the photosensitizer (FIGS. 2A-2B), allowing for the assumption that using a narrowband source (e.g., a laser) with a maximum at the absorption maximum of a photosensitizer, the same level of drug release as show in current results could be obtained using power density of 3-5 times less.

Example 4: Indirect Evaluation of Release of Liposomal Contents

Fluorescent Marker Release:

Release of the fluorescent marker calcein from the liposomes co-illuminated with the photosensitizer-peptide conjugate was shown by originally preparing liposomes with a very high self-quenching concentration of fluorophore and evaluating the increase of fluorescence of diluted samples upon dilution of released fluorophore in the total sample volume as described in Bisby R. H., Mead C., Morgan C. G., "Active uptake of drugs into photosensitive liposomes and rapid release on UV photolysis," (2000) Photochem. Photobiol. 72(1):57-61; Van Bambeke F., Kerkhofs A., Schanck A., Remade C., Sonveaux E., Tulkens P. M., Mingeot-Leclercq M. P., "Biophysical studies and intracellular destabilization of pH-sensitive liposomes," (2000) Lipids 35(2): 213-223.

Figure 5:
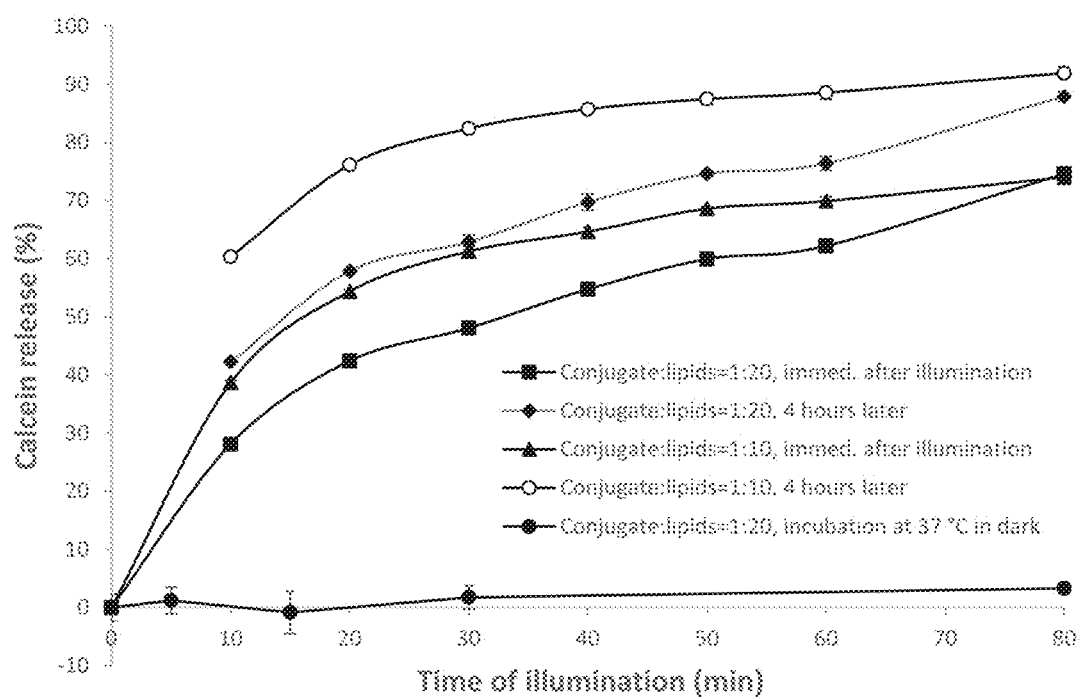
FIG. 5 shows a comparison of calcein release from liposomes co-illuminated with the photosensitizer-peptide conjugate at different conjugate:lipid ratios, immediately and 4 hours after illumination, against the control of liposomes co-incubated with the photosensitizer-peptide conjugate without illumination.
Figure 6:
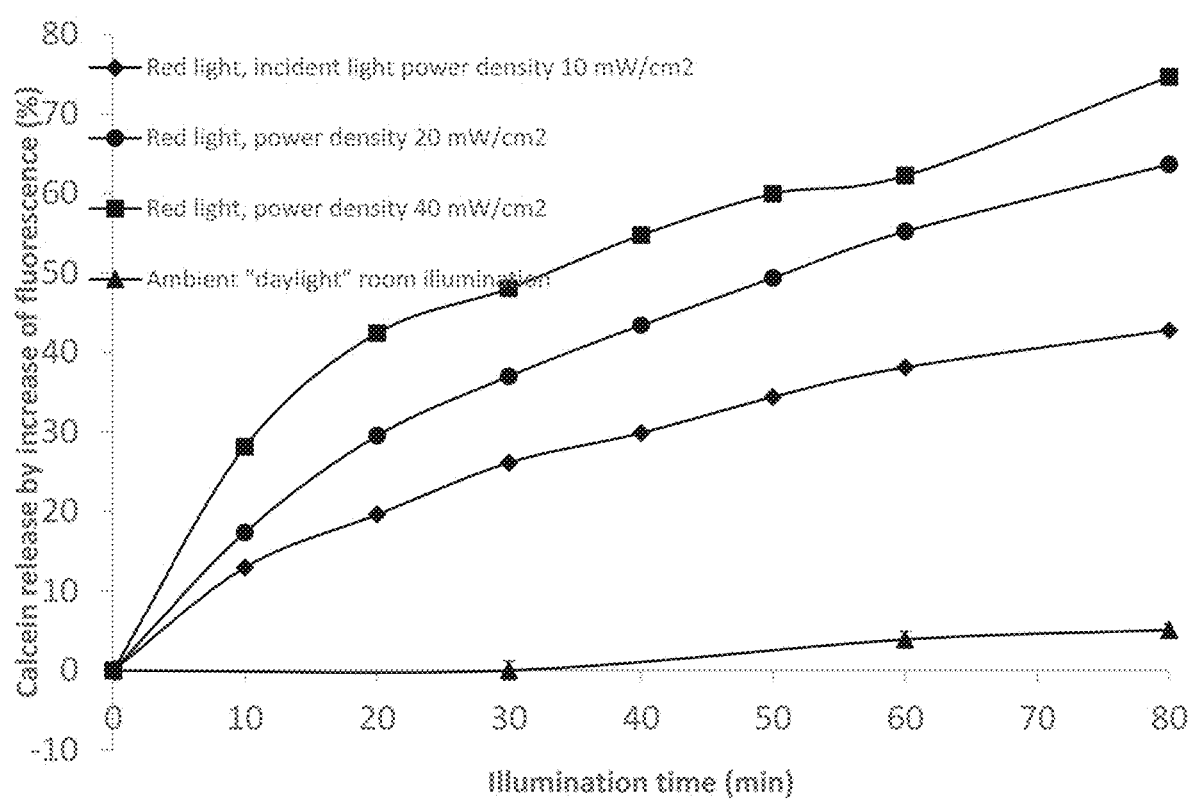
FIG. 6 shows a comparison of calcein release from liposomes co-illuminated with the photosensitizer-peptide conjugate at conjugate:lipid ratio of 1:20 with different light power density.

Co-illumination of calcein-loaded phosphatidylserine-supplied liposomes provided efficient release of calcein in direct dependence on the conjugate:lipid ratio, power density, and duration of illumination, while illumination without conjugate or treatment with conjugate without illumination (just timed co-incubation in the dark or incubation at 37° C.) did not have any significant effect (FIG. 5 and FIG. 6).

Drug Release:

Release of the drug substance (doxorubicin hydrochloride) from the liposomes was done by enhancement of its biological action (cytotoxicity) on cultured WI26-VA4 cells after pre-illuminating liposomes with or without photosensitizer-peptide conjugate in comparison to liposomes at the same dose without pre-illumination, co-incubated with cells for 4 hours. The extent of cell death was evaluated 48 hours after treatment using a MTT cell viability assay.

Figure 7:
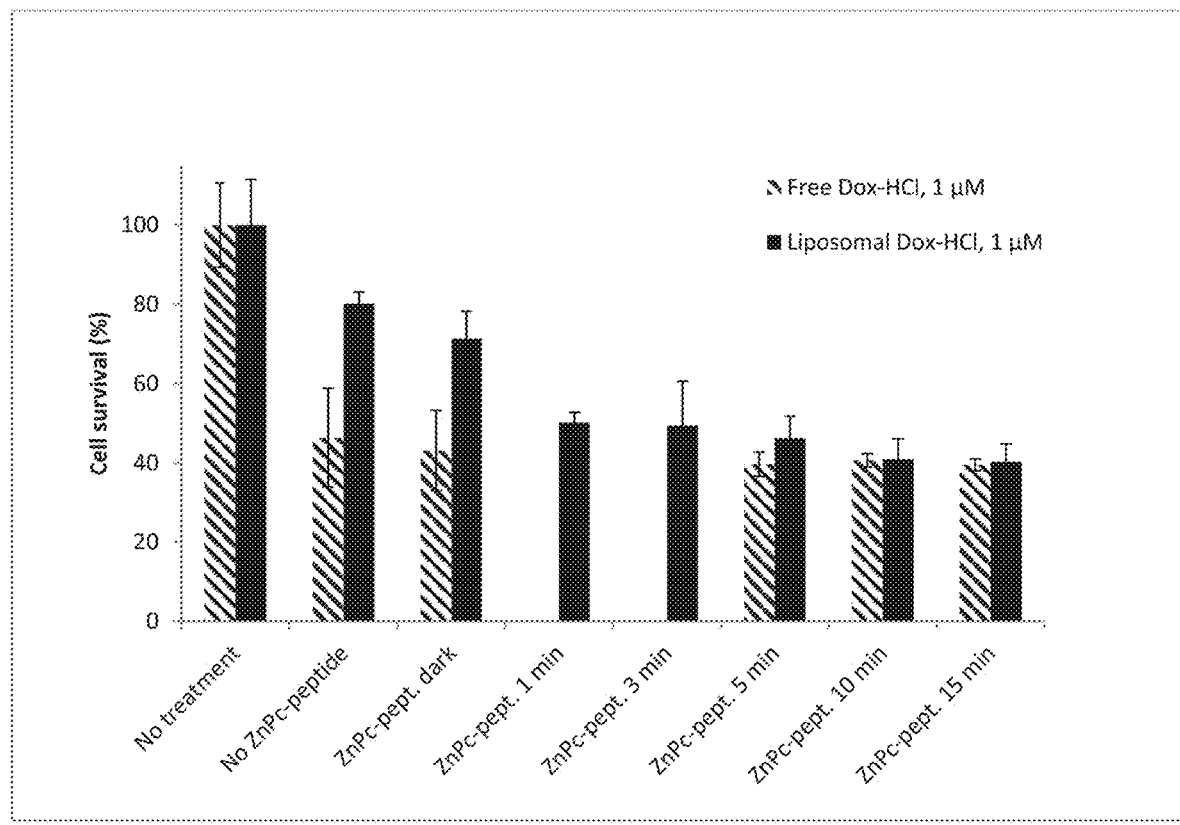
FIG. 7 shows a comparison of cytotoxicity of doxorubicin hydrochloride added to cells at an equal total dose of 1 μM in solution or encapsulated in liposomes, without or with co-illumination for different durations of time with a photosensitizer-peptide conjugate.

Preliminary tests of doxorubicin toxicity under the above-described conditions on WI26-VA4 cells showed that at a total dose of 1 μM, free doxorubicin hydrochloride caused about 60% cell death while liposome-encapsulated drug caused only about 20%. On the other hand, liposomes pre-illuminated with the photosensitizer-peptide conjugate showed significant enhancement of cytotoxicity, even with a short 1 min illumination; after 10 min of illumination, the level of cytotoxicity was equal to the free drug solution (FIG. 7).

Figure 8A:
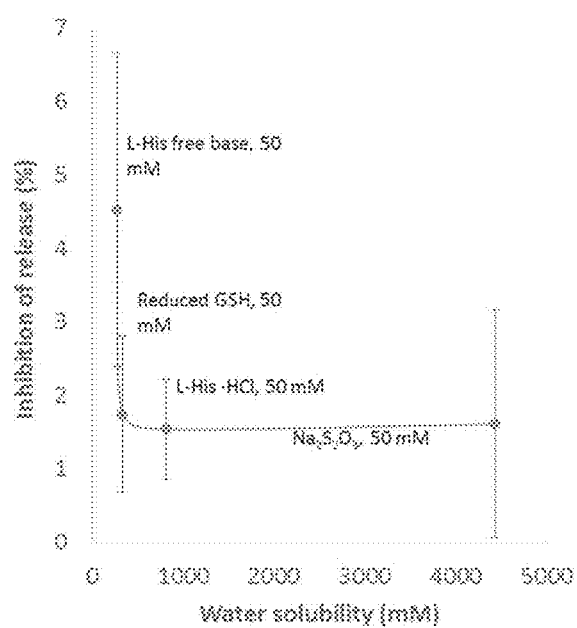
FIGS. 8A-8B show the inhibition of release of the encapsulated substance from the liposomal dispersion co-illuminated with the photosensitizer-peptide conjugate, in the presence of hydrophobic antioxidants (FIG. 8A) and hydrophilic antioxidants (FIG. 8B) of different water solubility.
Figure 8B:
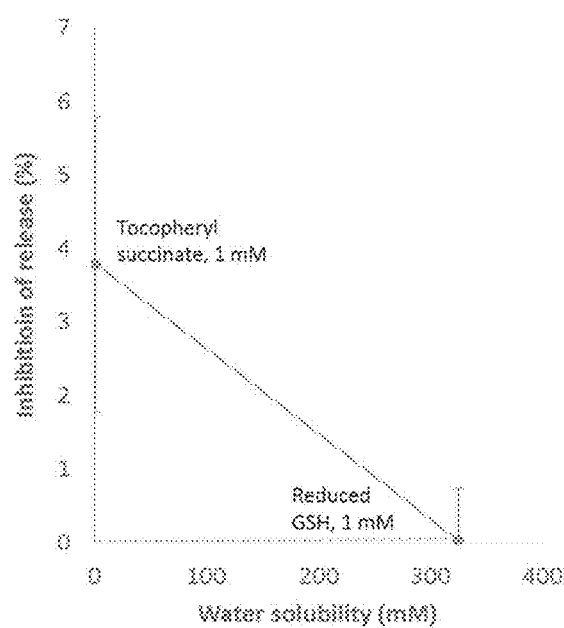
Figure 10A:
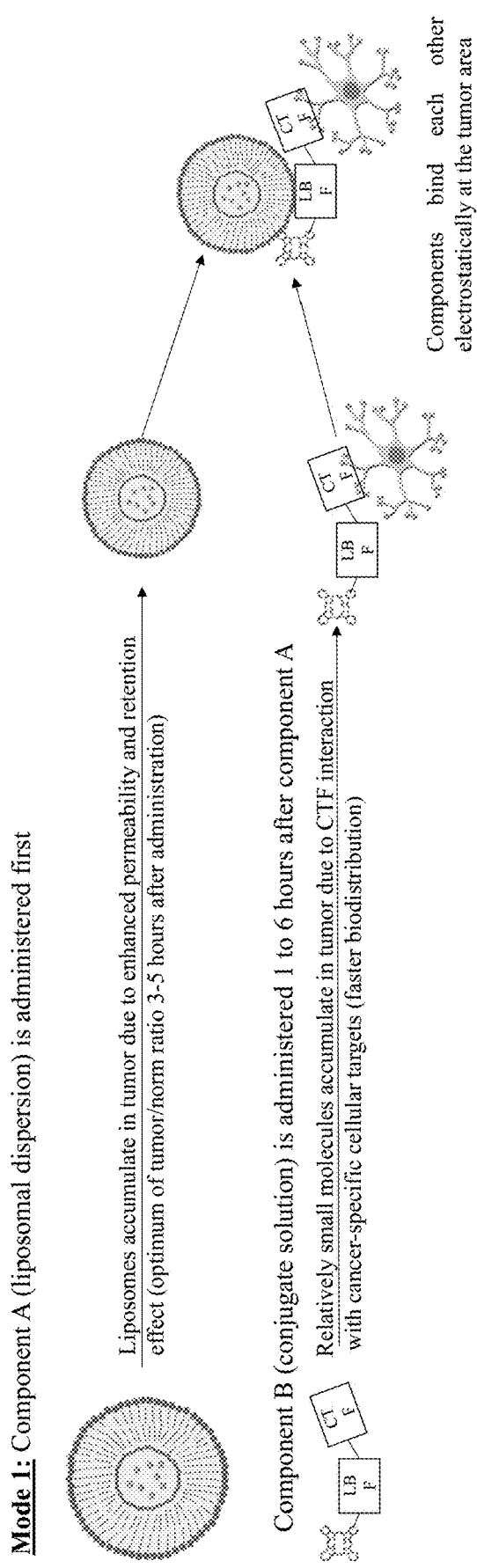
Figure 11:
FIG. 11 illustrates an exemplary embodiment of the method described herein.

Example 5: Study of Inhibition of Liposomal Release by Antioxidants of Different Hydrophilicity The photo-induced release of marker from calcein-loaded liposomes was performed as described above, along with the addition of nontoxic hydrophobic or hydrophilic antioxidants such as tocopheryl succinate (at 1 mM concentration), reduced glutathione (reduced GSH, at 1 mM or 50 mM), histidine amino acid in hydrochloride or free base form, as well as sodium thiosulfate (at 50 mM). The results showed that inhibition of load release in a liquid sample decreased with an increase in the water solubility of the antioxidant (FIGS. 8A-8B). With traditional ways of storing the liposomal drugs in lyophilized form, even hydrophilic antioxidants can be assumed to provide protection from oxidation during storage.

The invention claimed is:

1. A method of delivering a small molecule to a target tissue or organ of a subject in need thereof, comprising:
   a) administering a charged liposomal composition comprising a liposome and a small molecule encapsulated by the liposome to the subject, wherein the liposome comprises about 5 to about 30 mol % of an anionic phospholipid;
   b) administering a charged peptide composition comprising a peptide chain conjugated to a photosensitizer to the subject, wherein the peptide chain is from 14 to 40 amino acid residues total in length and comprises an amino acid sequence having at least 90% sequence identity to the sequence RLARLARRLARLAR (SEQ ID NO:1); and
   c) applying low intensity light to the subject to induce release of the small molecule from the liposome, wherein the intensity of the low intensity light is from about 10 mW/cm$^2$ to about 200 mW/cm$^2$;
   wherein the liposomal composition is negatively charged and the peptide composition is positively charged.

2. The method of claim 1, wherein the small molecule is a therapeutic agent.

3. The method of claim 2, wherein the therapeutic agent is a chemotherapeutic compound selected from the group consisting of bortezomib, cabozantinib-s-malate, camptothecin, capecitabine, ceritinib, daunorubicin, crizotinib, dabrafenib, dasatinib, degarelix, docetaxel, doxorubicin, doxorubicin hydrochloride, epirubicin, eribulin, etoposide, raloxifene, fulvestrant, methotrexate, pralatrexate, eribulin mesylate, topotecan, ibritumomab tiuxetan, ibrutinib, irinotecan, ixabepilone, cabazitaxel, ado-trastuzumab emtansine, leuprolide acetate, vincristine, mitomycin C, mitoxantrone, nelarabine, paclitaxel, prednisone, eltrombopag olamine, raloxifene hydrochloride, lenalidomide, omacetaxine mepesuccinate, bexarotene, temsirolimus, bendamustine hydrochloride, vinblastine sulfate, vincristine sulfate, vinorelbine tartrate, vorinostat, capecitabine, ipilimumab, goserelin acetate, carboplatin, cisplatin, gemcitabine, calicheamicin, 5-fluorouracil, actinomycin D, cyclophosphamide, vincristine, melphalan, and bleomycin.

4. The method of claim 3, wherein the chemotherapeutic compound is about 0.5% to about 10% by weight of the liposomal composition.

5. The method of claim 1, wherein the small molecule is a fluorescent marker.

6. The method of claim 1, wherein the peptide chain is from 14 to 20 amino acid residues total in length.

7. The method of claim 1, wherein the anionic phospholipid comprises two fatty acid chains that are each independently about 16 to about 20 carbons in length and have about 1 to about 4 double bonds per phospholipid molecule.

8. The method of claim 7, wherein the two fatty acid chains are the same.

9. The method of claim 7, wherein the anionic phospholipid is selected from a phosphatidylserine (PS), a phosphatidic acid, a phosphatidylglycerol, a phosphatidylethanolamine, bis(monoacylglycero)phosphate (BMP), 1-stearoyl-2-oleoyl-sn-glycero-3-phosphocholine, 1-stearoyl-2-oleoyl-sn-glycero-3-phosphoserine, and combinations thereof.

10. The method of claim 1, wherein the small molecule is hydrophilic.

11. The method of claim 10, wherein the small molecule is a hydrophilic chemotherapeutic agent.

12. The method of claim 11, wherein the chemotherapeutic agent is doxorubicin or doxorubicin hydrochloride.

13. The method of claim 10, wherein the small molecule is a hydrophilic fluorescent marker.

14. The method of claim 13, wherein the fluorescent marker is calcein.

15. The method of claim 1, wherein about 30% to about 50% of the amino acid residues of the positively charged peptide chain are arginine or other guanidinium-containing amino acid residue.

16. The method of claim 15, wherein at least 3 of the arginine or other guanidinium-containing amino acid residues are on the same side of the alpha-helix of the positively charged peptide chain.

17. The method of claim 1, wherein the photosensitizer is selected from the group consisting of derivatives of a porphyrin, a metalloporphyrin, a phthalocyanine, a metallophthalocyanine, a chalcogen pyrrillium dye, a pheophorbide, a pyropheophorbide, a pheophytin, a chlorin, a bacteriochlorin, a bacteriopheophorbide, a sapphyrin, a texaphyrin, a purpurin, a porphycene, a phenothiazinium, methylene blue, a xanthene dye, and optionally substituted dimeric or oligomeric porphyrin structures.

18. The method of claim 17, wherein the photosensitizer has about 1 to about 8 carboxyl groups.

19. The method of claim 18, wherein the photosensitizer has a maximum absorption band in the spectral range of about 660 to 860 nanometers.

20. The method of claim 18, wherein the photosensitizer has a quantum yield of singlet oxygen generation above about 0.3.

21. The method of claim 17, wherein the photosensitizer is zinc tetracarboxy phthalocyanine.

22. The method of claim 17, wherein the charged peptide composition comprises about one photosensitizer moiety and about 1 to about 8 peptide chains.

23. The method of claim 1, wherein the photosensitizer is attached to one end of the peptide chain and the peptide composition further comprises a targeting moiety at the end of the peptide chain opposite the photosensitizer.

24. The method of claim 23, wherein the targeting moiety is a peptide comprising about 4 to about 20 amino acid residues.

25. The method of claim 24, wherein the targeting moiety peptide comprises amino acid sequences selected from the group consisting of Ala-Glu-Tyr-Leu-Arg (SEQ ID NO:2), Tyr-Glu-Val-His-Thr-Tyr-Tyr-Leu-Asp (SEQ ID NO:3), Tyr-Val-Met-Gly-His-Phe-Arg-Trp-Asp-Arg-Phe (SEQ ID NO:4), Arg-Gly-Asp motif sequences, and Cys-Ser-Lys-Cys (SEQ ID NO: 5) motif sequences.

26. The method of claim 23, wherein the targeting moiety is able to bind to cell surface receptors on the target tissue or organ.

27. The method of claim 26, wherein the cell surface receptors are overexpressed on cancer cells.

28. The method of claim 1, wherein the liposomal composition and the peptide composition are administered at a ratio of about 40:1 to about 1:1 by weight, according to the dry weight of both compositions.

29. The method of claim 1, wherein the liposomal composition is administered before the peptide composition is administered.

30. The method of claim 29, wherein the liposomal composition is administered about 1 hour to about 6 hours before the peptide composition is administered.

31. The method of claim 1, wherein the liposomal composition and the peptide composition are administered at the same time.

* * * * *

UNITED STATES PATENT AND TRADEMARK OFFICE
CERTIFICATE OF CORRECTION

PATENT NO. : 11,154,619 B2
APPLICATION NO. : 15/900526
DATED : October 26, 2021
INVENTOR(S) : Meerovich et al.

It is certified that error appears in the above-identified patent and that said Letters Patent is hereby corrected as shown below:

On the Title Page

Item [56], Column 2, Line 9, delete "5:3546," and insert -- 5: 3546, --;

Item [56], Column 2, Line 11, delete "63:8126-8131,2003" and insert -- 63: 8126-8131, 2003 --;

Item [56], Column 2, Line 13, delete "3 5(2):" and insert -- 35(2): --;

Item [56], Column 2, Line 17, delete "Bioconj," and insert -- Bioconj. --; and

In the Claims

Column 29, Line 32, Claim 17, delete "pyrrillium" and insert -- pyrylium --.

Signed and Sealed this
Twenty-eighth Day of December, 2021

Drew Hirshfeld
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 5

<210> SEQ ID NO 1
<211> LENGTH: 14
<212> TYPE: PRT
<213> ORGANISM: Artificial
<220> FEATURE:
<223> OTHER INFORMATION: synthetic peptide

<400> SEQUENCE: 1

Arg Leu Ala Arg Leu Ala Arg Arg Leu Ala Arg Leu Ala Arg
1               5                   10

<210> SEQ ID NO 2
<211> LENGTH: 5
<212> TYPE: PRT
```

```
<213> ORGANISM: Artificial
<220> FEATURE:
<223> OTHER INFORMATION: synthetic peptide

<400> SEQUENCE: 2

Ala Glu Tyr Leu Arg
1               5

<210> SEQ ID NO 3
<211> LENGTH: 9
<212> TYPE: PRT
<213> ORGANISM: Artificial
<220> FEATURE:
<223> OTHER INFORMATION: synthetic peptide

<400> SEQUENCE: 3

Tyr Glu Val His Thr Tyr Tyr Leu Asp
1               5

<210> SEQ ID NO 4
<211> LENGTH: 11
<212> TYPE: PRT
<213> ORGANISM: Artificial
<220> FEATURE:
<223> OTHER INFORMATION: synthetic peptide

<400> SEQUENCE: 4

Tyr Val Met Gly His Phe Arg Trp Asp Arg Phe
1               5                   10

<210> SEQ ID NO 5
<211> LENGTH: 4
<212> TYPE: PRT
<213> ORGANISM: Artificial Sequence
<220> FEATURE:
<223> OTHER INFORMATION: synthetic peptide

<400> SEQUENCE: 5

Cys Ser Lys Cys
1
```